United States Patent [19]

Felix et al.

[11] Patent Number: 4,913,722

[45] Date of Patent: Apr. 3, 1990

[54] IMINOPHENYLTHIAZOLIDINES, PROCESS OF PREPARATION AND METHOD OF USE

[75] Inventors: Raymond A. Felix, Richmond; Jeffery T. Springer, LaHonda; Eugene G. Teach, El Cerrito; Frank X. Woolard, Berkeley, all of Calif.

[73] Assignee: ICI Americas Inc., Wilmington, Del.

[21] Appl. No.: 269,819

[22] Filed: Nov. 15, 1988

Related U.S. Application Data

[63] Continuation-in-part of Ser. No. 126,133, Nov. 17, 1987, abandoned, which is a continuation-in-part of Ser. No. 941,484, Dec. 15, 1986, abandoned.

[51] Int. Cl.[4] .................. C07D 277/18; A01N 43/78
[52] U.S. Cl. ........................ 71/90; 548/190; 548/193; 548/197; 548/198
[58] Field of Search ............ 548/190, 193, 197, 198; 71/90

[56] References Cited

U.S. PATENT DOCUMENTS

| | | | |
|---|---|---|---|
| 3,671,537 | 6/1972 | Toldy et al. | 548/190 |
| 3,804,848 | 4/1974 | Behner et al. | 548/190 |

FOREIGN PATENT DOCUMENTS

| | | | |
|---|---|---|---|
| 265162 | 4/1988 | European Pat. Off. | 548/225 |
| 43-18776 | 8/1968 | Japan | 548/190 |

OTHER PUBLICATIONS

Dains, et al., JACS 44, 2637 (1922).
Abdullaev et al., CA 91:151104s (1979).
Metzger, Thiazole and its Derivatives, part 1, 278–279 (date unknown).

Primary Examiner—Robert Gerstl
Attorney, Agent, or Firm—Joel G. Ackerman

[57] ABSTRACT

A 2-iminophenyl thiazolidine having the formula

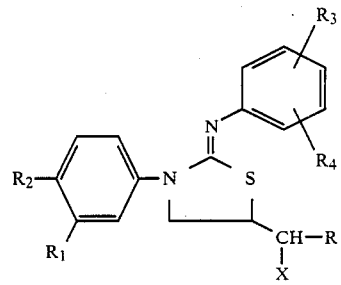

wherein R is hydrogen or methyl; $R_1$ is halo, nitro, cyano, $C_1$–$C_4$ alkyl, $C_1$–$C_4$ alkoxy, perhalomethyl, difluoromethyl, pentafluoroethyl, trifluoromethylthhio, difluoromethoxy, trifluoromethoxy, tetrafluoroethoxy, methylsulfonyl, $C_1$–$C_4$ alkyloxyiminomethyl, benzyloxyiminomethyl, 1-($C_1$–$C_4$ alkyl)-oxyiminoethyl or 1-benzyloxyiminoethyl; $R_2$ is hydrogen or halo; $R_3$ and $R_4$ are independently hydrogen, halo, nitro, cyano, $C_1$–$C_4$ haloalkyl, $C_1$–$C_4$ alkyl, $C_1$–$C_4$ fluoroalkoxy, $C_1$–$C_4$ alkoxy or $C_1$–$C_4$ alkylthio; and X is hydrogen or halogen.

Also disclosed is a process for making the compounds and a method of use which comprises applying the compound or composition to the locus where control is desired.

21 Claims, No Drawings

IMINOPHENYLTHIAZOLIDINES, PROCESS OF PREPARATION AND METHOD OF USE

CROSS-REFERENCE TO RELATED APPLICATIONS

This application is a continuation-in-part of application Ser. No. 126,133, filed Nov. 17, 1987, which in turn is a continaution-in-part of application Ser. No. 941,484, filed Dec. 15, 1986 both now abandoned.

BACKGROUND OF THE INVENTION

The present invention relates to certain iminophenylthiazolidine herbicide compounds, compositions, processes and methods of use.

There are a number of different types of herbicides presently sold commercially, and these fall into two general categories. The categories are pre-emergence and post-emergence herbicides. The pre-emergence herbicides are normally incorporated into or applied to the soil prior to the emergence of the weed plants from the soil, and the post-emergence herbicides are normally applied to plant surfaces after emergence of the weeds or other unwanted plants from the soil. Some herbicides are effective both as pre- and post-emergence herbicides. The iminophenylthiazolidines of this invention fall into that category.

DESCRIPTION OF THE INVENTION

It has now been discovered that certain 2-iminophenylthiazolidines have good herbicidal activity, when applied either pre- or post-emergence and used against annual and perennial grasses and broadleaf weeds.

As used herein, the term "herbicide" means a compound or composition which adversely controls or modifies the growth of plants. By the term "herbicidally effective amount" is meant any amount of such compound or composition which causes an adverse modifying effect upon the growth of plants. By "plants" is meant germinant seeds, emerging seedlings and established vegetation, including roots and above-ground portions. Such controlling or modifying effects include all deviations from natural development, such as killing, retardation, defoliation, desiccation, regulation, stunting, tillering, leaf burn, dwarfing, and the like.

The compounds of this invention are 2-iminophenylthiazolidines having the following formula:

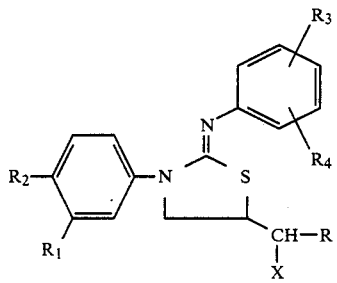

wherein

R is hydrogen or methyl;

$R_1$ is halo, nitro, cyano, $C_1$-$C_4$ alkyl, $C_1$-$C_4$ alkoxy, perhalomethyl, difluoromethyl, pentafluoroethyl, trifluoromethylthio, difluoromethoxy, trifluoromethoxy, tetrafluoroethoxy, methylsulfonyl, $C_1$-$C_4$ alkyloxyiminomethyl, benzyloxyiminomethyl, 1-($C_1$-$C_4$ alkyl)oxyiminoethyl or 1-benzyloxyiminoethyl;

$R_2$ is hydrogen or halo;

$R_3$ and $R_4$ are independently hydrogen, halo, nitro, cyano, $C_1$-$C_4$ haloalkyl, $C_1$-$C_4$ alkyl, $C_1$-$C_4$ fluoroalkoxy, $C_1$-$C_4$ alkoxy or $C_1$-$C_4$ alkylthio; and X is hydrogen or halogen.

The compositions of the invention comprise the aforementioned herbicide compounds, along with inert diluent carriers, as set forth more fully hereinbelow.

The method of the invention comprises the application to the locus where control is desired of either the compound(s) or composition containing the compound(s) described herein.

Representative compounds falling within the scope of the formula as set forth above include:

---

2-(4-cyano)phenylimino-3-(3-trifluoromethyl)phenyl-5-ethylthiazolidine 2-(3-trifluoromethyl)phenylimino-3-(3-trifluoromethyl)phenyl-5-ethylthia- zolidine 2-(3-chloro-4-fluoro)phenylimino-3-(3-trifluoromethyl)phenyl-5-ethylthia- zolidine 2-(4-chloro)phenylimino-3-(3-trifluoromethyl)phenyl-5-chloromethylthiazol- idine 2-(4-cyano)phenylimino-3-(3-trifluoromethyl)phenyl-5-chloromethylthiazol- idine 2-(3-chloro)phenylimino-3-(3-trifluoromethyl)phenyl-5-methylthiazolidine 2-(4-cyano)phenylimino-3-(3-chloro)phenyl-5-ethylthiazolidine 2-(3-chloro)phenylimino-3-(3-cyano)phenyl-5-ethylthiazolidine 2-(4-chloro)phenylimino-3-(3-cyano)phenyl-5-ethylthiazolidine

---

The compounds set forth above have been found to have especially good herbicidal activity against perennial and annual grasses and broadleaf weed species when applied as post-emergent herbicides.

The compounds of the invention can be produced by a multi-step reaction sequence which comprises reacting an N-alkenyl anilide with a suitable base to hydrolyze it to the alkenyl aniline. The alkenyl aniline is then combined with a suitable aryl isothiocyanate in the presence of a catalyst to form an N-alkenyl-N,N'-diaryl thiourea. The thiourea is in turn treated with a hydrogen or halogen ion source such as sulfuryl chloride or other suitable chloronium ion source to produce the thiazolidines of this invention.

This process can be illustrated generically in accordance with the following sequence of steps.

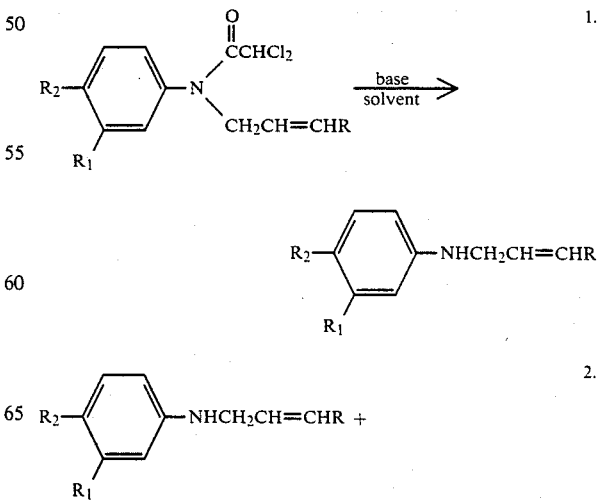

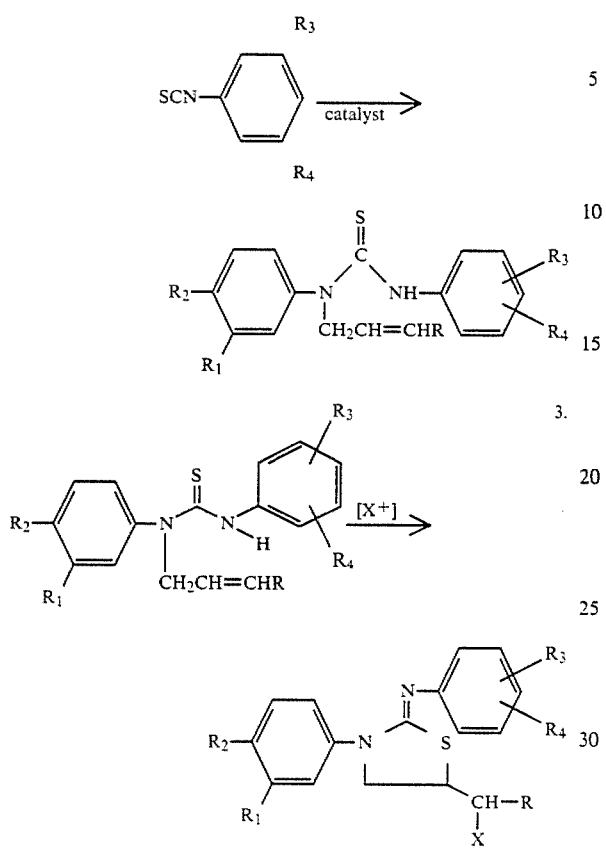

The reaction is conducted at ambient temperatures, preferably room temperature. The base used in step (1) set forth above, can be any of the normally used bases. However, potassium hydroxide is preferred. The catalyst used in step (2) is preferably dibutyl tin laurate, but other catalysts, such as diazobicyclooctane or triethylamine would also be suitable.

The hydrogen or halogen ion source set forth in step (3) is preferably sulfuryl chloride, but other ion sources, such as hydrochloric acid, trifluoromethanesulfonic acid and the like can be used.

Examples 1–5 below illustrate various methods of making the compounds of the invention using various starting materials.

EXAMPLE 1

Preparation of 2-(2-Chloro)phenylimino-3-(3-trifluoromethyl)phenyl-5-chloromethylthiazolidine To a five liter, round-bottomed flask, equipped with a mechanical stirrer, thermometer and 250 milliliter (ml) pressure equalizing funnel was added 468 grams (g) (1.5 mole) of N-allyl-N-(3-trifluoromethyl)phenyldichloroacetanilide and three liters of absolute ethanol. The mixture was stirred and 99 g (1.5 mole) of potassium hydroxide dissolved in 150 ml of water was added dropwise with stirring over a period of approximately 20 minutes. The temperature of the solution rose from 22° to 35° during this time and then gradually subsided. After 1.5 hours, chromatography showed the reaction to be completed. The solution was filtered to remove the precipitated potassium dichloroacetate and the solvent then removed in vacuo to give a semi-solid slurry. To the slurry was added 50 ml of ethyl acetate and the resulting suspension was again filtered to remove the precipitated acetate. The solvent was then removed in vacuo to give a dark oil that was distilled at aspirator pressure to provide 275.5 g (90%) of N-allyl-3-aminobezotrifloride as a colorless oil, b.p. 100°–105° C.

Next, 9.07 g (45.1 mmole) of N-allyl-3-aminobenzotrifluoride was combined neat with 7.65 g (45.1 mmole) of 2-chlorophenylisothiocyanate and 1 drop of dibutyl tin dilaurate in a 100 ml round-bottomed flask equipped with a magnetic stirrer. A stopper was put in the flask and the solution was stirred at room temperature. After three days the resulting thick oil was chromatographed on a short silica gel column (eluent 2:1 $CH_2Cl_2$/hexanes) to obtain 11.55 g (69%) of a thiourea product, $C_{17}H_{14}ClF_3N_2$.

Next, 2.10 g (5.66 mole) of the thiourea compound obtained as above was dissolved in 50 ml of dry (passed over alumina) $CH_2Cl_2$ and placed in a 100 ml round-bottomed flask equipped with a magnetic stirrer. The flask was then placed in a water bath at 20° C. and the contents stirred. A solution of 0.77 g (5.70 mmol) of $SO_2Cl_2$ in 10 ml of dry $CH_2Cl_2$ was then added dropwise over 5 minutes and when the addition was complete the stirring was continued for an additional 0.5 hour. The solution was then washed with two 70 ml portions of 1M $NaHCO_3$ solution, dried ($Na_2SO_4$) and the solvent removed in vacuo. Chromatography of the residual oil on silica gel with 2:1 hexane/$CH_2Cl_2$ as eluent afforded 2.10 g (91%) of 2-(2-chloro)-phenylimino-3-(3-trifluoromethyl)phenyl-5-chloromethylthiazolidine.

EXAMPLE 2

Preparation of 2-(3-Chloro)phenylimino-3-(3-trifluoromethyl)phenyl-5-chloromethylthiazolidine 9.07 g (45.1 mmole) of N-allyl-3-aminobenzotrifluoride produced in accordance with Example 1 was combined neat with 7.65 g (45.1 mmole) of 3-chlorophenylisothiocyanate and 1 drop of dibutyl tin dilaurate in a 100 ml round-bottomed flask equipped with a magnetic stirrer. A stopper was put in the flask and the solution stirred at room temperature over the weekend. After three days the resulting thick syrup was chromatographed on a short silica gel column (eluent 2:1 $CH_2Cl_2$/hexanes) to obtain 16.72 g (100%) of $C_{17}H_{14}ClF_3N_2S$, N-allyl-N-(3-trifluoromethyl)phenyl-N'-(3-chloro)phenyl thiourea, as a light brownish-orange solid.

2.10 g (5.66 mmole) of the thiourea compound formed as in the previous paragraph was dissolved in 50 ml of dry (passed over alumina) $CH_2Cl_2$ and placed in a 100 ml round-bottomed flask equipped with a magnetic stirrer. The flask was then placed in a water bath at 20° C. and the contents stirred. A solution of 0.77 g (5.70 mmol) of $SO_2Cl_2$ in 10 ml of dry $CH_2Cl_2$ was then added dropwise over 5 minutes and when the addition was complete the stirring was continued for an additional 0.5 hour. The solution was then washed with two 70 ml portions of 1M $NaHCO_3$, dried ($Na_2SO_4$) and the solvent removed in vacuo. Chromatography of the residual oil on silica gel with 2:1 hexane/$CH_2Cl_2$ as eluent afforded 1.73 g (75%) of product as a thick syrup.

EXAMPLE 3

Preparation of
2-(4-Chloro)phenylimino-3-(3-trifluoromethyl)phenyl-5-chloromethylthiazolidine Eight grams (39.8 mmole) of N-allyl-3-aminobenzotrifluoride, produced in Example, 1 in 5 ml acetonitrile was combined with 7.65 g (45.1 mmole) of 4-chlorophenylisothiocyanate and 1 drop of dibutyl tin dilaurate in a 100 ml round-bottomed flask equipped with a magnetic stirrer. A stopper was put in the flask and the solution stirred at room temperature. After approximately 150 hours, the solvent was removed in vacuo and the residual oil was chromatographed on a short silica gel column (eluent 2:1 $CH_2Cl_2$/hexane then 100% $CH_2Cl_2$) to obtain 10.25 g (69%) of $C_{17}H_{14}ClF_3N_2S$, N-allyl-N-(3-trifluoromethyl)phenyl-N'-3-chlorophenyl thiourea.

Two grams (5.39 mmole) of the thiourea formed as above in 50 ml of dry (passed over alumina) $CH_2Cl_2$ was added to a 100 ml round-bottomed flask equipped with a magnetic stirrer. The flask was then placed in a water bath at 20° C. and the contents stirred. As solution of 0.73 g (5.41 mmol) of $SO_2Cl_2$ in 10 ml of dry $CH_2Cl_2$ was then added dropwise over 5 minutes and when the addition was complete the stirring was continued for an additional 7 hours. The solution was then washed with two 50 ml portions of saturated $K_2CO_3$, dried ($Na_2SO_4$) and the solvent removed in vacuo. Chromatography of the residual oil on silica gel with 2:1 hexanes/$CH_2Cl_2$ as eluent afforded 2.10 g (96%) of the subject compound, identified as such by suitable analytical techniques.

EXAMPLE 4

Preparation of
2-(3-Trifluoromethyl-4-chloro)phenylimino-3-3-(trifluoromethyl)phenyl-5-chloromethylthiazolidine 8.00 g (39.8 mmole) of N-allyl-3-aminobenzotrifluoride was combined with 9.46 g (39.8 mmole) of 4-chloro-3-trifluoromethylphenylisothiocyanate and 1 drop of dibutyl tin dilaurate in a 100 ml round-bottomed flask equipped with a magnetic stirrer. A stopper was put in the flask and the solution stirred at room temperature. After stirring for approximately 150 hours, the crude product was chromatographed on a short silica gel column (eluent 2:1 $CH_2Cl_2$/hexanes then 100% $CH_2Cl_2$) to obtain 16.20 g (93%) of a thiourea of the formula $C_{18}H_{13}ClF_6N_2S$.

Two grams (4.56 mmole) of the thiourea formed as in the paragraph immediately preceding in 50 ml of dry (passed over alumina) $CH_2Cl_2$ was added to a 100 ml round-bottomed flask equipped with a magnetic stirrer. The flask was then placed in a water bath at 20° C. and the contents stirred. A solution of 0.62 g (4.59 mmol) of $SO_2Cl_2$ in 10 ml dry of $CH_2Cl_2$ was then added dropwise over 5 minutes and when the additions were complete the stirring was continued for a total of about 5 days. The solution was then washed with two 50 ml portions of saturated $K_2CO_3$, dried ($Na_2SO_4$) and the solvent removed in vacuo. Chromatography of the residual oil on silica gel with 2:1 hexanes/$CH_2Cl_2$ as eluent afforded 2.12 g (98%) of product, which was identified as such by suitable analytical procedures.

EXAMPLE 5

Preparation of
2-Phenylimino-3-(3-trifluoromethyl)phenyl-5-ethyl-thiazolidine

A quantity of 3-trifluoromethylphenyl-N-crotyl-N'-phenyl thiourea was prepared in accordance with the same general procedure set forth in paragraph (2) of Example 1 above. 2.10 grams (5.99 mmoles) of the thiourea were dissolved in 100 ml of ethylene dichloride in a 250 ml round-bottomed flask equipped with a magnetic stirrer and nitrogen bubbler. Trifluoromethanesulfonic acid (0.90 g, 5.99 mmoles) was added all at once and the mixture allowed to stir under nitrogen overnight. After approximately 18 hours, the reaction mixture was washed with 3×50 ml saturated potassium carbonate solution, dried with sodium sulfate and the solvent removed in vacuo to give a residual oil. The residual oil was chromatographed by medium pressure liquid chromatography with 30% ethyl acetate, 70% hexane as eluent. Removal of the solvent in vacuo gave 1.45 g (69%) of product, 2-phenylimino-3-(3-trifluoromethyl)phenyl-5-ethylthiazolidine.

The compounds of the invention can also be prepared in accordance with a process which is another aspect of the invention which comprises reacting:

(a) an aryl substituted isocyanate of the formula

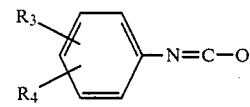

and (b) an anilino alcohol of the formula

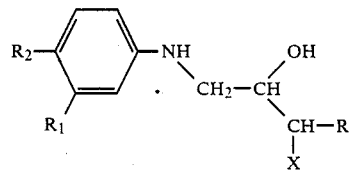

at a temperature and for a period of time sufficient to cause substantial completion of the reaction to form (c) an intermediate urea alcohol of the formula

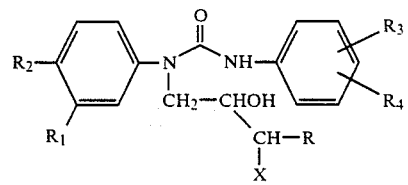

and (d) reacting said intermediate urea alcohol with a thiophosphorus anhydride and continuing said reaction at a sufficient temperature and for a sufficient period of time to cause ring closure to form the end product

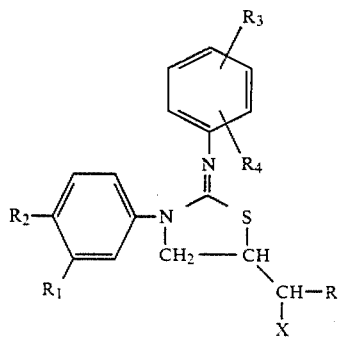

wherein X, R, $R_1$, $R_2$, $R_3$ and $R_4$ are as previously defined.

Each of the starting compounds used in the process of this invention can either be purchased commercially or prepared by using techniques known in the literature.

For example, the isocyanates (a) with which the anilino alcohols (b) are reacted are either commercially available or can be made by standard techniques.

The anilino alcohol (b), is made by the reaction of an aniline with an epoxide. This procedure is described in co-pending Application Ser. No. 864,238, filed May 19, 1986, now U.S. Pat. No. 4,723,986.

In the anilino alcohol, the alkyl group (R) is preferably methyl.

The thiophosphorus anhydride which makes available the sulfur atom for inclusion in the ring is preferably phosphorus pentasulfide. Other thiophosphorus anhydrides which also make available the sulfur atom for inclusion into the ring structure of the end product at the place indicated, such as 2,4-bisphospha-2,4-diethyl-2,4-dithiono-1,3-dithiaetane (also known as 2,4-bis(ethyl)-1,3-dithia-2,4-α-phosphetane-2,4-disulfide), could be used.

The reaction sequence for the process of this invention can be represented as follows.

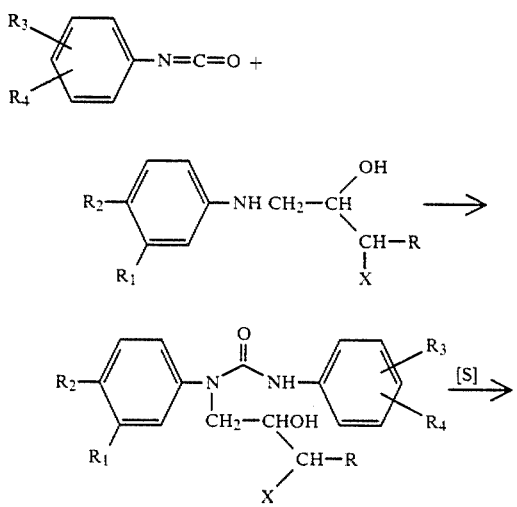

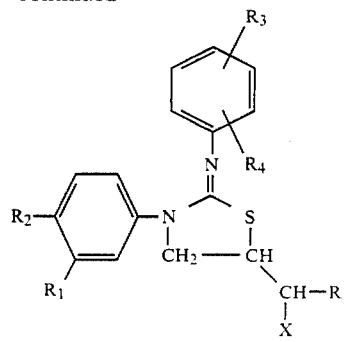

wherein X, R, $R_1$, $R_2$, $R_3$ and $R_4$ are as previously defined and [S] is a thiophosphorus anhydride.

The cyclization reaction which forms the final product is conducted in the presence of an inert solvent, preferably an aliphatic or aromatic hydrocarbon solvent (e.g., hexane, heptane, benzene, toluene, xylenes, mesitylenes) or an ether (e.g., acyclic ethers such as diethyl ether or cyclic ethers such as tetrahydrofuran or dioxanes). Of these, aromatic hydrocarbons and cyclic ethers are preferred. The reaction is conducted at a temperature of from about 0° C. to about 180° C., preferably from about 60° C. to about 120° C., and is generally conducted at the reflux temperature of the solvent. The reaction is also conducted preferably at atmospheric pressure and for a sufficient period of time to allow completion of the reaction. In general, this will range from about 1 to about 8 hours.

In general, the reactants used in the process of this invention are used in substantially equivalent molar ratios. Excess reactants can be used. However, in general, this does not increase the yield of end products to any significant degree.

The process of this invention will be more fully understood by reference to the following examples, which are intended to be illustrative of the process of the invention, but not limiting thereof. The products were identified by suitable analytical techniques, such as IR, NMR and MS.

EXAMPLE 6

Preparation of 2-(4-Chloro)phenylimino-3-(3-trifluoromethyl)phenyl 5-ethyl thiazolidine A round-bottomed flask was obtained, equipped with an addition funnel and thermometer. Into this flask was combined 2.3 grams (g) (0.01 mole) of 1-(3-trifluoromethyl)anilino-2-butanol, 1.5 g (0.01 mole) of 4-chlorophenyl isocyanate in 10 milliliters (ml) of toluene. This mixture was stirred at room temperature for approximately 1 hour, until the isocyanate peak disappeared from the IR spectrum. The compound in solution was 1-(3-trifluoromethyl)phenyl-1-(2'-hydroxy)butyl, 3-(4-chloro)phenyl urea.

Thereafter, 2.2 g phosphorus pentasulfide (0.01 mole) was added to the solution in one portion. The solution was heated to reflux and maintained at reflux for approximately 2 hours. Thereafter, 100 ml of water was added, followed by 100 ml of ether, and the phases separated, then the organic phase was washed with 100 ml of one molar NaOH. The phases were separated, the organic layer was dried over magnesium sulfate and evaporated to dryness to yield 3.0 g of product, identified as such as suitable analytical techniques.

EXAMPLE 7

Preparation of 2-(4-Chloro)phenylimino-3-(3-trifluoromethyl)phenyl 5-ethyl thiazolidine The same technique was repeated as in Example 6, using the same amounts of reagents, except that instead of phosphorus pentasulfide being utilized, 2.8 g of 2,4-bisphospha-2,4-diethyl-2,4-dithiono-1,3-dithietane was used. The product was detected by GC/MS.

EXAMPLE 8

Preparation of 2-(4-Nitro)phenylimino-3-(3-trifluoromethyl)phenyl-5-ethyl thiazolidine To a round-bottom flask were added 7.0 g (0.03 mole) of 1-(3-trifluoromethyl)anilino-2-butanol, 50 ml of toluene and 5.02 g (0.03 mole) of 4-nitrophenyl isocyanate. The solution was heated at reflux 4.5 hours and overnight. The next day 2 g of product were removed for analysis, then 5.55 g (0.025 mole) phosphorus pentasulfide ($P_2S_5$) were added. The mixture was refluxed another 1 hour then allowed to cool and stand overnight. The mixture was diluted with 100 ml diethyl ether and stirred 0.5 hour with 200 ml of 1 molar (M) sodium hydroxide (NaOH) then phase separated. The organic phase was dried over magnesium sulfate and evaporated under reduced pressure to yield 9.15 g of the subject thiazolidine. Structure was confirmed by spectroscopic analyses.

EXAMPLE 9

Preparation of 2-(3-Methylthio)phenylimino-3-(3-trifluoromethyl)phenyl-5-ethyl thiazolidine In a round-bottom flask were added 8.10 g (0.0203 mole) of 1-(m-trifluoromethyl)phenyl-1-(2'-hydroxybutyl)-3-(3-methylthio)phenyl urea, 150 ml of toluene and 4.52 g (0.02 mole) of phosphorus pentasulfide. The solution was refluxed 0.5 hour. The mixture was washed with 1M sodium hydroxide and isolated as in Example 3 to yield 4.25 g of the subject thiazolidine. The structure was confirmed by spectroscopic analyses.

EXAMPLE 10

Preparation of 2-(3-Chloro-4-fluoro)phenylimino-3-(3-trifluoromethyl)phenyl-5-ethyl thiazolidine The techniques of Example 8 were employed based on a 0.0472M scale, using the same proportions of reagents, except that 8.09 g (0.0472 mole) of 3-chloro, 4-fluoro phenyl isocyanate instead of 4-nitrophenyl isocyanate was utilized, and refluxed 1 hour. 17.73 g of the thiazolidine were obtained and the structure was confirmed by spectroscopic analyses.

EXAMPLE 11

Preparation of 2-(2-Fluoro)phenylimino-3-(3-trifluoromethyl)-phenyl-5-ethyl thiazolidine The techniques of Example 8 were employed using the same molar quantities of reagents and 2-fluorophenyl isocyanate instead of 4-nitrophenyl isocyanate. The mixture was refluxed 0.5 hour after the $P_2S_5$ addition. The product of this reaction was chromatographed on silica using 30% ethyl acetate/70% hexanes and evaporated under reduced pressure to yield 6.81 g of the thiazolidine which were confirmed by spectroscopic analyses.

EXAMPLE 12

Preparation of 2-(4-trifluoromethoxy)phenylimino-3-(3-trifluoromethyl)phenyl-5-ethyl thiazolidine The techniques of Example 9 were employed based on a 0.0159 scale using the same proportions of reagents, 6.95 g (0.0159 mole) of 2-(m-trifluoromethyl)phenyl-1-(2-hydroxybutyl)-3-(4-trifluoromethoxy)-phenyl urea, 150 ml of toluene and 3.54 g (0.016 mole) of $P_2S_5$. The mixture was refluxed 45 minutes. The product was isolated as in Example 8 to yield 4.95 g of the thiazolidine. The structure was confirmed by IR, NMR and MS.

The same general techniques were used to make the additional compounds which are set forth in Table I below wherein X, R, $R_1$, $R_2$, $R_3$ and $R_4$ are as indicated.

TABLE I

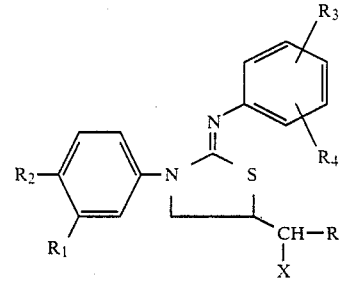

| Compound No. | R | $R_1$ | $R_2$ | $R_3$ | $R_4$ | X | $n_D^{30}$ or m.p. °C. |
|---|---|---|---|---|---|---|---|
| 1 | H | $CF_3$ | H | p-$NO_2$ | H | H | 171–172 |
| 2 | H | $CF_3$ | H | p-CN | H | H | 122–130 |
| 3 | H | $CF_3$ | H | m-$CF_3$ | p-Cl | H | thick syrup |
| 4 | H | $CF_3$ | H | o-Cl | p-$CH_3$ | H | thick syrup |
| 5 | $CH_3$ | $CF_3$ | H | p-CN | H | H | 98–99 |
| 6 | $CH_3$ | $CF_3$ | H | p-Cl | H | H | 64–67 |
| 7 | $CH_3$ | $CF_3$ | H | m-F | H | H | 1.5845 |
| 8 | $CH_3$ | $CF_3$ | H | p-F | H | H | 80–84.5 |
| 9 | $CH_3$ | $CF_3$ | H | m-Cl | H | H | thick syrup |
| 10 | $CH_3$ | $CF_3$ | H | H | H | H | thick syrup |
| 11 | $CH_3$ | $CF_3$ | H | m-$CF_3$ | H | H | thick syrup |
| 12 | $CH_3$ | $CF_3$ | H | p-$CF_3$ | H | H | 65–70 |
| 13 | $CH_3$ | $CF_3$ | H | m-CN | H | H | thick syrup |
| 14 | $CH_3$ | $CF_3$ | H | m-Br | H | H | 1.6055 |
| 15 | $CH_3$ | $CF_3$ | H | m-Cl | p-Cl | H | thick syrup |
| 16 | $CH_3$ | $CF_3$ | H | m-Cl | p-F | H | 1.5941 |
| 17 | $CH_3$ | $CF_3$ | H | o-Cl | p-Cl | H | thick syrup |
| 18 | $CH_3$ | $CF_3$ | H | 3-Cl | 5-Cl | H | thick syrup |
| 19 | $CH_3$ | $CF_3$ | H | m-$CF_3$ | p-Cl | H | 1.5762 |
| 20 | H | $CF_3$ | H | o-Cl | H | Cl | 1.5762 |
| 21 | H | $CF_3$ | H | m-Cl | H | Cl | 1.5762 |
| 22 | H | $CF_3$ | H | p-Cl | H | Cl | 100.5–103 |
| 23 | H | $CF_3$ | H | o-F | H | Cl | thick syrup |
| 24 | H | $CF_3$ | H | m-F | H | Cl | thick syrup |
| 25 | H | $CF_3$ | H | m-$NO_2$ | H | Cl | thick syrup |
| 26 | H | $CF_3$ | H | p-$NO_2$ | H | Cl | 123.5–127 |
| 27 | H | $CF_3$ | H | p-CN | H | Cl | waxy solid |
| 28 | H | $CF_3$ | H | m-$CF_3$ | p-Cl | Cl | thick syrup |
| 29 | H | $CF_3$ | H | o-Cl | p-$CH_3$ | Cl | thick syrup |
| 30 | H | $CF_3$ | H | m-$CF_3$ | H | H | 69–72 |
| 31 | H | $CF_3$ | H | o-Cl | H | H | 1.6061 |
| 32 | H | $CF_3$ | H | m-Cl | H | H | 98–100 |
| 33 | H | $CF_3$ | H | p-Cl | H | H | 149–165 |
| 34 | H | $CF_3$ | H | o-F | H | H | thick syrup |
| 35 | H | $CF_3$ | H | m-F | H | H | 83–86 |
| 36 | H | $CF_3$ | H | m-$NO_2$ | H | H | thick syrup |

TABLE I-continued

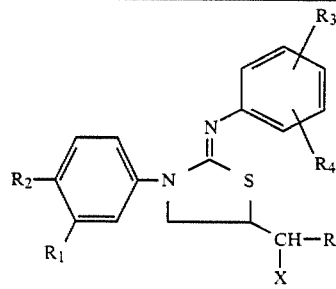

| Compound No. | R | $R_1$ | $R_2$ | $R_3$ | $R_4$ | X | $n_D^{30}$ or m.p. °C. |
|---|---|---|---|---|---|---|---|
| 37 | $CH_3$ | $CF_3$ | H | o-$CH_3$ | p-Cl | H | waxy solid |
| 38 | $CH_3$ | Cl | H | p-Cl | H | H | 1.6484 |
| 39 | $CH_3$ | Cl | H | p-CN | H | H | thick syrup |
| 40 | $CH_3$ | Cl | H | m-Br | H | H | thick syrup |
| 41 | $CH_3$ | Cl | H | m-$CF_3$ | p-Cl | H | 1.6126 |
| 42 | $CH_3$ | Cl | H | m-Cl | p-Cl | H | thick syrup |
| 43 | $CH_3$ | CN | H | p-Cl | H | H | thick syrup |
| 44 | $CH_3$ | CN | H | m-Cl | H | H | thick syrup |
| 45 | H | $CF_3$ | H | p-F | H | H | 105.5–109.5 |
| 46 | H | $CF_3$ | H | m-Cl | p-Br | H | thick syrup |
| 47 | H | $CF_3$ | H | p-Br | H | H | thick syrup |
| 48 | H | $CF_3$ | H | o-F | p-F | H | 52–56 |
| 49 | H | $CF_3$ | H | o-F | H | H | 1.5821 |
| 50 | H | CN | H | m-Cl | H | H | thick syrup |
| 51 | $CH_3$ | $CF_3$ | H | m-$NO_2$ | H | H | thick syrup |
| 52 | $CH_3$ | $CF_3$ | H | p-$SCH_3$ | H | H | thick syrup |
| 53 | $CH_3$ | $CF_3$ | H | m-$SCH_3$ | H | H | thick syrup |
| 54 | $CH_3$ | $CF_3$ | H | p-$OCF_3$ | H | H | thick syrup |
| 55 | $CH_3$ | $CF_3$ | H | p-$OCH_3$ | H | H | thick syrup |
| 56 | $CH_3$ | $CF_3$ | H | m-$OCH_3$ | H | H | thick syrup |
| 57 | $CH_3$ | $SCF_3$ | H | p-F | H | H | thick syrup |
| 58 | $CH_3$ | $CF_3$ | H | p-$NO_2$ | H | H | waxy solid |
| 59 | H | $CF_3$ | H | p-CN | H | Cl | 76–80 |
| 60 | H | $CF_3$ | H | p-F | H | Cl | 105–110 |
| 61 | H | $CF_3$ | H | p-CN | H | H | thick syrup |

The herbicidal activity of representative compounds of the invention was tested in accordance with the following procedures.

HERBICIDAL ACTIVITY TESTS

Test No. 1

This test offers herbicidal activity test data to show the effectiveness of the compounds of the invention against various weed species. The effect is observed by comparing the extent of weed control in test flats treated with the compounds against that occurring in similar control flats. All are applied at 4.0 lb/A (4.48 kg/ha) to a pre-emergence and a post-emergence screening flat. An 80 gal/A (748.3 l/ha) spray volume is utilized. Post-emergence flats are seeded 12 days prior to treatment. Pre-emergence flats are seeded one day prior to treatment. Overhead watering of pre-emergence flats and soil surface watering of post-emergence flats, so as to avoid wetting the foliage, is carried out for the duration of the test.

Weed seeds are planted in a 6×10×3 inch (15.25×7.6 cm) aluminum flat at a seed depth of 0.5 inch (1.3 cm). Soil for flats is prepared using Keeton sandy loam soil fortified with 17-17-17 fertilizer (N-$P_2O_5$-$K_2O$ on a weight basis) and Captan 80W. The test weeds were as follows:

| COMMON NAME | SCIENTIFIC NAME | ABR |
|---|---|---|
| Broadleaf Weeds: | | |
| annual morning glory | Ipomoea purpurea | AMG |
| velvetleaf | Abutilon theophrasti | VL |
| mustard | Brassica sp. | MD |
| curly dock | Rumex crispus | CD |
| Grasses: | | |
| yellow nutsedge | Cyperus exculentus | YNS |
| foxtail | Setaria sp. | FT |
| watergrass | Echinochloa crusgalli | WG |
| wild oat | Avena Fatua | WO |

The spray solution is prepared by dissolving 240 mg of herbicide compound in 20 ml of acetone containing 1% Tween ® 20 (polyoxy ethylene sorbitan monolaurate), then adding 20 ml of water to the resulting solution. The stock solutions are applied using a linear spray table. The table is calibrated to deliver 80 gal/A (748.3 l/ha) of spray solution using an 8004E teejet nozzle set 18 inches (45.7 cm) from the surface. Pre-emergence flats are raised to the level of the post-emergence foliage canopy by setting the flats on a wooden block.

In both instances, either pre- or post-emergent testing, approximately 18 days after treatment, the degree of weed control was estimated and recorded as percentage control compared to the growth of the same species in an untreated check flat of the same age. The rating scale ranges from 0 to 100%, where 0 equals no effect with plant growth equal to the untreated control, and 100 equals complete kill.

The results are listed in the Table below.

TABLE II

GREENHOUSE HERBICIDE TEST RESULTS

| Cmpd. No. | Application Rate (lb/A) | Method | FT | WG | WO | AMG | VL | MD | CD | YNS |
|---|---|---|---|---|---|---|---|---|---|---|
| 1 | 4.00 | PES | 100 | 80 | 70 | 90 | 90 | 100 | N | 0 |
|   | 4.00 | POS | 60 | 40 | 40 | 80 | 90 | 100 | N | 0 |
| 2 | 4.00 | PES | 95 | 75 | 30 | 60 | 70 | 100 | 35 | 0 |
|   | 4.00 | POS | 40 | 40 | 35 | 50 | 60 | 40 | 50 | 0 |
| 4 | 4.00 | PES | 100 | 20 | 10 | 60 | 30 | 100 | N | 0 |
|   | 4.00 | POS | 20 | 20 | 20 | 60 | 80 | 100 | N | 0 |
| 7 | 4.00 | PES | 100 | 100 | 85 | 98 | 100 | 100 | N | 0 |
|   | 4.00 | POS | 60 | 70 | 50 | 50 | 80 | 70 | N | 10 |
| 8 | 4.00 | PES | 100 | 100 | 95 | 100 | 100 | 100 | N | 0 |
|   | 4.00 | POS | 100 | 100 | 95 | 100 | 100 | 100 | N | 100 |
| 9 | 4.00 | PES | 100 | 90 | 50 | 50 | 40 | 100 | 35 | 0 |
|   | 4.00 | POS | 90 | 90 | 65 | 100 | 100 | 95 | 95 | 0 |
| 10 | 4.00 | PES | 100 | 100 | 80 | 50 | 50 | 100 | 50 | 0 |
|    | 4.00 | POS | 90 | 50 | 35 | 75 | 85 | 50 | 30 | N |
| 11 | 4.00 | PES | 100 | 100 | 90 | 80 | 100 | 100 | N | 0 |
|    | 4.00 | POS | 100 | 80 | 60 | 100 | 100 | 100 | N | 0 |
| 12 | 4.00 | PES | 100 | 100 | 80 | 100 | 100 | 100 | N | 0 |
|    | 4.00 | POS | 80 | 80 | 80 | 50 | 90 | 65 | N | 0 |

TABLE II-continued

GREENHOUSE HERBICIDE TEST RESULTS

| Cmpd. No. | Application Rate (lb/A) | Method | Percent Injury | | | | | | | |
|---|---|---|---|---|---|---|---|---|---|---|
| | | | FT | WG | WO | AMG | VL | MD | CD | YNS |
| 13 | 4.00 | PES | 100 | 100 | 80 | 100 | 85 | 100 | N | 0 |
| | 4.00 | POS | 80 | 50 | 40 | 80 | 100 | 100 | N | 0 |
| 14 | 4.00 | PES | 100 | 80 | 80 | 100 | 100 | 100 | N | 0 |
| | 4.00 | POS | 85 | 80 | 80 | 80 | 80 | 80 | N | 0 |
| 15 | 4.00 | PES | 100 | 85 | 80 | 100 | 100 | 100 | N | 0 |
| | 4.00 | POS | 100 | 100 | 80 | 90 | 95 | 100 | N | 0 |
| 16 | 4.00 | PES | 100 | 100 | 85 | 100 | 95 | 100 | N | 0 |
| | 4.00 | POS | 100 | 100 | 00 | 100 | 100 | 100 | N | 0 |
| 17 | 4.00 | PES | 100 | 80 | 80 | 95 | 100 | 100 | N | 0 |
| | 4.00 | POS | 100 | 50 | 30 | 90 | 90 | 100 | N | 0 |
| 18 | 4.00 | PES | 100 | 80 | 50 | 80 | 85 | 100 | N | 0 |
| | 4.00 | POS | 100 | 50 | 30 | 80 | 80 | 100 | N | 0 |
| 19 | 4.00 | PES | 100 | 80 | 80 | 85 | 90 | 100 | N | 0 |
| | 4.00 | POS | 100 | 80 | 80 | 95 | 90 | 100 | N | 0 |
| 20 | 4.00 | PES | 20 | 10 | 0 | 10 | 20 | 20 | 0 | 0 |
| | 4.00 | PES | 0 | 0 | 60 | 10 | 35 | 65 | 50 | 0 |
| 21 | 4.00 | PES | 35 | 10 | 10 | 65 | 40 | 85 | 35 | 0 |
| | 4.00 | POS | N | N | N | N | N | N | N | N |
| 22 | 4.00 | PES | 70 | 70 | 20 | 20 | 25 | 50 | 20 | 0 |
| | 4.00 | POS | 30 | 20 | 25 | 50 | 50 | 80 | 70 | 0 |
| 23 | 4.00 | PES | 70 | 60 | 20 | 10 | 20 | 85 | 20 | 0 |
| | 4.00 | POS | 15 | 20 | 10 | 35 | 35 | 50 | 75 | 0 |
| 24 | 4.00 | PES | 100 | 85 | 35 | 80 | 50 | 95 | 85 | 0 |
| | 4.00 | POS | 70 | 40 | 35 | 75 | 50 | 85 | 80 | 0 |
| 25 | 4.00 | PES | 90 | 75 | 25 | 25 | 40 | 80 | 75 | N |
| | 4.00 | POS | 100 | 60 | 25 | 70 | 40 | 90 | 70 | 10 |
| 26 | 4.00 | PES | 30 | 30 | 0 | 10 | 20 | 85 | 30 | 0 |
| | 4.00 | POS | 15 | 10 | 0 | 25 | 20 | 50 | 50 | 0 |
| 27 | 4.00 | PES | 90 | 75 | 35 | 40 | 25 | 75 | 0 | 0 |
| | 4.00 | POS | 30 | 35 | 30 | 30 | 25 | 40 | 25 | N |
| 28 | 4.00 | PES | 80 | 70 | 30 | 20 | 20 | 75 | 20 | N |
| | 4.00 | POS | 80 | 25 | 25 | 35 | 20 | 40 | 65 | N |
| 29 | 4.00 | PES | 40 | 0 | 0 | 10 | 0 | 50 | 0 | 0 |
| | 4.00 | POS | 15 | 10 | 0 | 70 | 60 | 80 | 25 | 0 |
| 30 | 4.00 | PES | 90 | 75 | 25 | 10 | 25 | 75 | 0 | 0 |
| | 4.00 | POS | 60 | 40 | 35 | 95 | 100 | 85 | 65 | N |
| 31 | 4.00 | PES | 100 | 40 | 30 | 85 | 80 | 100 | N | 0 |
| | 4.00 | POS | 100 | 30 | 30 | 30 | 30 | 100 | N | 0 |
| 32 | 4.00 | PES | 100 | 85 | 70 | 40 | 80 | 100 | N | 0 |
| | 4.00 | POS | 80 | 20 | 10 | 80 | 90 | 100 | N | 0 |
| 34 | 4.00 | PES | 100 | 95 | 30 | 60 | 60 | 100 | N | 0 |
| | 4.00 | POS | 100 | 90 | 20 | 90 | 85 | 100 | N | 0 |
| 35 | 4.00 | PES | 100 | 85 | 80 | 60 | 90 | 100 | N | 0 |
| | 4.00 | POS | 80 | 30 | 20 | 60 | 85 | 100 | N | 0 |
| 37 | 4.00 | PES | 100 | 85 | 80 | 100 | 75 | 100 | N | 0 |
| | 4.00 | POS | 100 | 80 | 80 | 60 | 80 | 100 | N | 0 |
| 38 | 4.00 | PES | 100 | 80 | 75 | 100 | 100 | 100 | N | 0 |
| | 4.00 | POS | 80 | 60 | 40 | 65 | 80 | 70 | N | 0 |
| 39 | 4.00 | PES | 100 | 100 | 80 | 100 | 100 | 100 | N | 0 |
| | 4.00 | POS | 80 | 80 | 60 | 90 | 100 | 100 | N | 0 |
| 40 | 4.00 | PES | 100 | 85 | 80 | 25 | 85 | 100 | N | 0 |
| | 4.00 | POS | 95 | 60 | 30 | 50 | 90 | 80 | N | 0 |
| 41 | 4.00 | PES | 100 | 50 | 50 | 50 | 90 | 100 | N | 100 |
| | 4.00 | POS | 90 | 20 | 20 | 20 | 60 | 100 | N | 0 |
| 42 | 4.00 | PES | 100 | 85 | 60 | 90 | 100 | 100 | N | 0 |
| | 4.00 | POS | 80 | 30 | 80 | 40 | 90 | 100 | N | 0 |
| 43 | 4.00 | PES | 100 | 85 | 65 | N | 95 | N | N | 0 |
| | 4.00 | POS | 25 | 50 | 35 | N | 75 | N | N | 0 |
| 44 | 4.00 | PES | 100 | 100 | 40 | 100 | 100 | N | N | 0 |
| | 4.00 | POS | 100 | 100 | 100 | 100 | 100 | N | N | 35 |
| 45 | 4.00 | PES | 100 | 80 | 60 | 20 | 20 | 90 | N | 0 |
| | 4.00 | POS | 60 | 40 | 30 | 60 | 80 | 80 | N | 0 |
| 46 | 4.00 | PES | 100 | 80 | 70 | 85 | 95 | 100 | N | 0 |
| | 4.00 | POS | 70 | 60 | 60 | 50 | 80 | 80 | N | 0 |
| 47 | 4.00 | PES | 100 | 90 | 80 | 90 | 100 | 100 | N | 0 |
| | 4.00 | POS | 70 | 50 | 40 | 95 | 95 | 100 | N | 0 |
| 48 | 4.00 | PES | 100 | 100 | 80 | 100 | 90 | 100 | N | 0 |
| | 4.00 | POS | 100 | 85 | 90 | 90 | 90 | 90 | N | 0 |
| 49 | 4.00 | PES | 100 | 95 | 80 | 40 | 60 | 60 | N | 0 |
| | 4.00 | POS | 100 | 60 | 60 | 90 | 90 | 90 | N | N |
| 50 | 4.00 | PES | 100 | 80 | 80 | 60 | 80 | 100 | N | 0 |
| | 4.00 | POS | 90 | 70 | 50 | 90 | 100 | 100 | N | 0 |
| 51 | 4.00 | PES | 100 | 90 | 80 | 40 | 60 | 100 | N | 0 |
| | 4.00 | POS | 80 | 60 | 60 | 60 | 80 | 80 | N | 0 |
| 52 | 4.00 | PES | 100 | 90 | 50 | 80 | 100 | 100 | N | 0 |
| | 4.00 | POS | 60 | 60 | 60 | 60 | 80 | 80 | N | 0 |
| 53 | 4.00 | PES | 100 | 50 | 50 | 100 | 100 | 100 | N | 0 |

TABLE II-continued
GREENHOUSE HERBICIDE TEST RESULTS

| Cmpd. No. | Application Rate (lb/A) | Method | Percent Injury | | | | | | | |
|---|---|---|---|---|---|---|---|---|---|---|
| | | | FT | WG | WO | AMG | VL | MD | CD | YNS |
| | 4.00 | POS | 30 | 40 | 30 | 60 | 80 | 80 | N | 0 |
| 54 | 4.00 | PES | 100 | 85 | 60 | 60 | 90 | 100 | N | 0 |
| | 4.00 | POS | 90 | 80 | 80 | 80 | 90 | 90 | N | 0 |
| 55 | 4.00 | PES | 100 | 100 | 60 | 75 | 90 | 100 | N | 0 |
| | 4.00 | POS | 80 | 75 | 60 | 60 | 80 | 80 | N | 0 |
| 56 | 4.00 | PES | 100 | 80 | 50 | 60 | 100 | 100 | N | 0 |
| | 4.00 | POS | 80 | 50 | 50 | 60 | 80 | 80 | N | 0 |
| 57 | 4.00 | PES | 100 | 100 | 100 | 80 | 100 | 100 | N | 0 |
| | 4.00 | POS | 80 | 80 | 80 | 80 | 80 | 80 | N | 10 |
| 58 | 4.00 | PES | 40 | 5 | 5 | 50 | 5 | 5 | N | 0 |
| | 4.00 | POS | 5 | 10 | 5 | 80 | 40 | 20 | N | 0 |
| 59 | 4.00 | PES | 100 | 90 | 90 | 100 | 100 | 100 | N | 0 |
| | 4.00 | POS | 100 | 50 | 50 | 100 | 100 | 100 | N | 30 |
| 60 | 4.00 | PES | 100 | 90 | 75 | 80 | 100 | 100 | N | 0 |
| | 4.00 | POS | 100 | 60 | 60 | 60 | 90 | 100 | N | 0 |
| 61 | 4.00 | PES | 100 | 100 | 85 | 100 | 100 | 100 | N | 0 |
| | 4.00 | POS | 80 | 60 | 60 | 60 | 100 | 100 | N | 30 |

N = Not tested.
PES = Pre-emergence.
POS = Post-emergence.

Test No. 2

Another series of tests was undertaken in accordance with the procedure described above in Test 1, except that differing quantities of herbicide were used. Those quantities were achieved by dilution of the original spray solution.

| The weed species were as follows: | | |
|---|---|---|
| green foxtail | *Setaria viridis* | FT |
| annual ryegrass | *Lolium multiflorum* | ARG |
| watergrass | *Echinochloa crusgalli* | WG |
| shattercane | *Sorghum bicolor* | SHC |
| wild oat | *Avena fatua* | WO |
| broadleaf signalgrass | *Bracharia platyphylla* | BSG |
| annual morningglory | *Ipomoea purpurea* | AMG |
| cocklebur | *Xanthium pensylvanicum* | CB |
| hemp sesbania | *Sesbania exaltata* | SESB |
| velvetleaf | *Abutilon theophrasti* | VL |
| sicklepod | *Cassia obtusifolia* | SP |
| yellow nutsedge | *Cyperus esculentus* | YNS |

In addition to the foregoing weed species, the herbicides were also tested against various crop species. The crop species were as follows:

| | | |
|---|---|---|
| soybean | *Glycine max* | SOY |
| milo | *Sorghum bicolor* | ML |
| rice | *Oryzae sativa* | RC |
| sugarbeet | *Beta vulgaris* | SB |
| corn | *Zea mays* | SN |
| cotton | *Gossypium hirsutum* | COT |
| wheat | *Triticum aestivum* | WH |

The results of these tests are set forth in Table III below.

TABLE III

| Cmpd. No. | Application Rate lb/A | Method | Weed Species Percent Injury | | | | | | | | | | | | | | Crop Plants | | | | | |
|---|---|---|---|---|---|---|---|---|---|---|---|---|---|---|---|---|---|---|---|---|---|---|
| | | | FT | ARG | WG | SHC | WO | BSG | AMG | CB | SESB | VL | SP | YNS | SOY | WH | ML | RC | SB | CN | COT |
| 1 | 0.25 | PES | 50 | 10 | 25 | 25 | 0 | 25 | 0 | 0 | 0 | 0 | 0 | 0 | 0 | 0 | 0 | 0 | 0 | 0 | 0 |
| | 0.50 | PES | 90 | 10 | 0 | 0 | 0 | 10 | 0 | 0 | 0 | 0 | 0 | 0 | 10 | 0 | 0 | 0 | 20 | 0 | 35 |
| | 1.00 | PES | 95 | 15 | 15 | 20 | 10 | 15 | 15 | 0 | 20 | 0 | 20 | 0 | 20 | 0 | 0 | 25 | 0 | 0 | 0 |
| | 0.25 | POS | 0 | 0 | 0 | 0 | 0 | 0 | 10 | 0 | 10 | 25 | 20 | 0 | 0 | 0 | 20 | 0 | 0 | 0 | 15 |
| | 0.50 | POS | 0 | 0 | 0 | 0 | 0 | 0 | 20 | 0 | 30 | 15 | 20 | 0 | 20 | 0 | 10 | 0 | 0 | 15 | 15 |
| | 1.00 | POS | 0 | 5 | 5 | 5 | 0 | 5 | 15 | 30 | 10 | 10 | 20 | 0 | 25 | 5 | 5 | 0 | 0 | 0 | 10 |
| 3 | 0.25 | PES | 100 | 5 | 5 | 5 | 5 | 5 | 30 | 50 | 30 | 10 | 0 | 0 | 0 | 0 | 0 | 0 | 80 | 0 | 0 |
| | 0.50 | PES | 100 | 30 | 5 | 5 | 10 | 5 | 60 | 50 | 50 | 20 | 0 | 0 | 5 | 5 | 5 | 0 | 100 | 0 | 5 |
| | 1.00 | PES | 100 | 90 | 10 | 10 | 50 | 40 | 60 | 70 | 80 | 20 | 0 | 0 | 0 | 0 | 0 | 0 | 100 | 0 | 10 |
| 4 | 0.25 | PES | 0 | 0 | 0 | 0 | 0 | 0 | 0 | 0 | 0 | 0 | 0 | 0 | 0 | 0 | 0 | 0 | 0 | 0 | 5 |
| | 0.50 | PES | 10 | 0 | 0 | 0 | 10 | 0 | 15 | 60 | 30 | 50 | 0 | 0 | 30 | 0 | 0 | 0 | 0 | 10 | 0 |
| | 1.00 | PES | 5 | 0 | 0 | 0 | 10 | 10 | 20 | 60 | 50 | 50 | 0 | 30 | 30 | 0 | 5 | 0 | 30 | 10 | 30 |
| 5 | 0.20 | POS | 10 | 0 | 10 | 20 | 20 | 10 | 20 | 75 | 70 | 50 | 0 | 70 | 30 | 5 | 15 | 10 | 30 | 20 | 30 |
| | 0.25 | PES | 10 | 30 | 20 | 10 | 40 | 30 | 40 | 80 | 80 | 60 | 0 | 70 | 40 | 0 | 20 | 0 | 30 | 30 | 40 |
| | 0.50 | POS | 20 | 50 | 20 | 10 | 10 | 10 | 80 | 30 | 30 | 10 | 10 | 0 | 5 | 5 | 30 | 10 | 30 | 0 | 40 |
| 6 | 0.05 | PES | 100 | 50 | 20 | 20 | 20 | 50 | 80 | 98 | 98 | 40 | 20 | 0 | 10 | 15 | 15 | 0 | 100 | 0 | 30 |
| | 0.10 | PES | 100 | 80 | 60 | 30 | 60 | 80 | 100 | 100 | 100 | 95 | 60 | 0 | 25 | 15 | 20 | 10 | 100 | 5 | 25 |
| | 0.25 | PES | 100 | 90 | 90 | 30 | 70 | 100 | 100 | 100 | 100 | 40 | 0 | 0 | 40 | 50 | 40 | 0 | 100 | 15 | 30 |
| | 0.50 | PES | 100 | 100 | 100 | 30 | 80 | 100 | 100 | 100 | 100 | 40 | 40 | 0 | 70 | 0 | 5 | 10 | 100 | 30 | 60 |
| | 1.00 | PES | 100 | 100 | 100 | 60 | 95 | 100 | 100 | 100 | 100 | 95 | 50 | 0 | 20 | 0 | 10 | 0 | 30 | 80 | 90 |
| | 2.00 | PES | 100 | 10 | 5 | 5 | 0 | 0 | 30 | 40 | 40 | 40 | 40 | 70 | 20 | 0 | 10 | 10 | 30 | 5 | 100 |
| | 0.20 | POS | 10 | 5 | 10 | 5 | 10 | 10 | 30 | 40 | 50 | 60 | 50 | 80 | 30 | 5 | 10 | 10 | 30 | 0 | 40 |
| | 0.10 | POS | 50 | 50 | 20 | 5 | 30 | 20 | 40 | 80 | 80 | 60 | 60 | 30 | 20 | 0 | 10 | 10 | 30 | 5 | 40 |
| | 0.50 | POS | 50 | 50 | 20 | 10 | 30 | 10 | 50 | 60 | 80 | 60 | 20 | 70 | 40 | 5 | 20 | 10 | 30 | 30 | 40 |
| | 1.00 | POS | 75 | 50 | 20 | 10 | 50 | 40 | 60 | 85 | 85 | 80 | 25 | 80 | 40 | 0 | 20 | 0 | 40 | 25 | 60 |
| | 2.00 | POS | 30 | 30 | 10 | 10 | 30 | 30 | 50 | 70 | 70 | 90 | 65 | 80 | 40 | 5 | 20 | 10 | 50 | 30 | 65 |
| 7 | 0.25 | PES | 100 | 50 | 50 | 20 | 20 | 60 | 60 | 20 | 50 | 90 | 40 | 0 | 5 | 5 | 5 | 0 | 30 | 10 | 40 |
| | 0.50 | PES | 100 | 95 | 85 | 70 | 80 | 80 | 40 | 50 | 95 | 100 | 50 | 5 | 10 | 0 | 10 | 0 | 80 | 10 | 10 |
| | 1.00 | PES | 100 | 100 | 100 | 20 | 80 | 90 | 20 | 75 | 100 | 90 | 60 | 20 | 15 | 5 | 20 | 0 | 100 | 20 | 30 |
| | 0.25 | POS | 100 | 30 | 5 | 5 | 5 | 5 | 70 | 0 | 0 | 90 | 0 | 5 | 10 | 5 | 5 | 0 | 50 | 0 | 80 |
| | 0.50 | POS | 100 | 30 | 10 | 20 | 30 | 10 | 20 | 0 | 100 | 100 | 5 | 20 | 20 | 5 | 5 | 5 | 100 | 5 | 5 |
| | 1.00 | POS | 100 | 30 | 65 | 20 | 80 | 50 | 70 | 0 | 100 | 100 | 40 | 0 | 0 | 10 | 5 | 5 | 100 | 30 | 10 |
| 9 | 0.25 | PES | 40 | 40 | 50 | 20 | 30 | 40 | 100 | 50 | 80 | 80 | 50 | 0 | 0 | 0 | 0 | 0 | 30 | 10 | 20 |
| | 0.50 | PES | 40 | 40 | 50 | 20 | 30 | 40 | 40 | 50 | 90 | 80 | 50 | 0 | 25 | 0 | 10 | 5 | 30 | 5 | 25 |
| | 1.00 | PES | 50 | 50 | 50 | 30 | 40 | 50 | 60 | 60 | 90 | 80 | 60 | 0 | 30 | 25 | 10 | 25 | 100 | 30 | 40 |
| 12 | 0.25 | PES | 95 | 85 | 75 | 0 | 20 | 50 | 75 | 15 | 40 | 40 | 20 | 0 | 25 | 25 | 35 | 5 | 30 | 35 | 35 |
| 13 | 0.50 | PES | 100 | 100 | 95 | 40 | 35 | 65 | 50 | 0 | 50 | 50 | 25 | 90 | 30 | 15 | 30 | 15 | 40 | 25 | 35 |
| | 0.25 | POS | 100 | N | Z | 75 | 50 | 90 | 100 | 25 | 50 | 65 | 35 | 35 | 30 | 20 | 15 | 20 | 50 | 15 | 75 |
| | 0.50 | POS | 20 | 20 | N | 20 | 25 | Z | 20 | 20 | 50 | 50 | 65 | 50 | 15 | 35 | 0 | 35 | 100 | 25 | 75 |
| 14 | 0.25 | POS | 30 | 35 | 20 | 20 | 25 | 30 | 60 | 100 | 60 | 40 | 35 | 20 | 20 | 20 | 0 | 0 | 50 | 0 | 10 |
| | 0.50 | POS | 10 | 10 | 5 | 0 | 10 | 20 | 35 | 80 | 90 | 80 | 40 | 0 | 10 | 0 | 20 | 10 | 20 | 40 | 30 |
| | 1.00 | POS | 10 | 10 | 10 | 5 | 20 | 20 | 40 | 50 | 50 | 80 | 50 | 0 | 30 | 0 | 0 | 5 | 50 | 5 | 5 |
| | 0.25 | PES | 100 | 20 | 10 | 10 | 40 | 50 | 60 | N | 20 | 80 | 50 | 0 | 5 | 0 | 5 | 0 | 100 | 5 | 20 |
| | 0.50 | PES | 100 | 60 | 30 | 20 | 20 | 65 | 20 | Z | 95 | 95 | 90 | 0 | 5 | 0 | 5 | 0 | 100 | 0 | 20 |
| | 1.00 | PES | 100 | 85 | 40 | 10 | 50 | 75 | 40 | Z | 95 | 100 | 95 | 0 | 5 | 5 | 5 | 0 | 100 | 5 | 20 |

TABLE III-continued

| Cmpd. No. | Application Rate lb/A | Application Method | FT | ARG | WG | SHC | WO | BSG | AMG | CB | SESB | VL | SP | YNS | SOY | WH | ML | RC | SB | CN | COT |
|---|---|---|---|---|---|---|---|---|---|---|---|---|---|---|---|---|---|---|---|---|---|
| 15 | 0.25 | PES | 100 | 50 | 15 | 0 | 10 | 10 | 40 | 30 | 30 | 10 | 0 | 0 | 5 | 0 | 0 | 0 | 100 | 0 | 20 |
|  | 0.50 | PES | 100 | 95 | 65 | 20 | 30 | 30 | 85 | 80 | 80 | 10 | 0 | 0 | 10 | 5 | 5 | 0 | 100 | 0 | 20 |
|  | 1.00 | PES | 100 | 98 | 8 | 020 | 70 | 60 | 100 | 100 | 100 | 65 | 0 | 0 | 20 | 50 | 10 | 0 | 100 | 0 | 50 |
|  | 0.25 | PES | 100 | 80 | 10 | 10 | 20 | 30 | 85 | 98 | 98 | 40 | 0 | 20 | 20 | 5 | 5 | 0 | 100 | 0 | 25 |
|  | 0.50 | PES | 100 | 98 | 40 | 30 | 70 | 50 | 100 | 100 | 100 | 90 | 0 | 50 | 40 | 15 | 10 | 0 | 100 | 0 | 50 |
|  | 1.00 | PES | 100 | 98 | 98 | 50 | 85 | 95 | 100 | 100 | 100 | 98 | 0 | 0 | 50 | 20 | 5 | 0 | 100 | 50 | 90 |
| 17 | 0.25 | PES | 95 | 10 | 5 | 5 | 0 | 0 | 10 | 20 | 30 | 50 | 0 | 0 | 5 | 0 | 5 | 0 | 100 | 0 | 5 |
|  | 0.50 | PES | 100 | 10 | 5 | 5 | 5 | 5 | 30 | 70 | 40 | 10 | 0 | 0 | 5 | 0 | 5 | 0 | 100 | 0 | 5 |
|  | 1.00 | PES | 100 | 40 | 30 | 10 | 20 | 30 | 80 | 80 | 80 | 20 | 0 | 10 | 10 | 0 | 5 | 0 | 30 | 5 | 20 |
|  | 0.25 | POS | 0 | 0 | 0 | 0 | 0 | 0 | 20 | 50 | 30 | 40 | 0 | 0 | 10 | 0 | 0 | 0 | 50 | 5 | 20 |
|  | 0.50 | POS | 0 | 0 | 0 | 0 | 5 | 5 | 20 | 50 | 30 | 50 | 0 | 10 | 10 | 0 | 0 | 0 | 50 | 10 | 25 |
|  | 1.00 | POS | 0 | 5 | 5 | 0 | 0 | 5 | 20 | 50 | 30 | 50 | 0 | 20 | 5 | 0 | 0 | 0 | 80 | 0 | 50 |
| 18 | 0.25 | PES | 95 | 10 | 0 | 0 | 0 | 10 | 0 | 10 | 10 | 5 | 0 | 0 | 5 | 0 | 0 | 0 | 0 | 0 | 0 |
|  | 0.50 | PES | 100 | 20 | 10 | 5 | 10 | 30 | 10 | 85 | 20 | 10 | 95 | 0 | 5 | 0 | 0 | 0 | 20 | 0 | 5 |
|  | 1.00 | PES | 100 | 80 | 20 | 40 | 30 | 40 | 80 | 5 | 80 | 30 | N | 0 | 10 | 10 | 0 | 0 | 50 | 0 | 5 |
| 19 | 0.50 | PES | 10 | 10 | 40 | 15 | 40 | 20 | 60 | N | 100 | 95 | N | 0 | 0 | 0 | 0 | 0 | 20 | 0 | 15 |
| 21 | 1.00 | POS | 90 | 20 | 25 | 15 | 40 | 80 | N | N | N | N | N | 0 | 0 | 0 | 0 | 0 | 10 | 0 | 0 |
|  | 2.00 | PES | 100 | 30 | 60 | 25 | 40 | 90 | 55 | N | 90 | 45 | 60 | 0 | 0 | 0 | 0 | 0 | 20 | 0 | 25 |
| 24 | 0.50 | PES | 100 | 20 | 45 | 30 | 15 | 85 | 15 | Z | 65 | 0 | 30 | 0 | 20 | 0 | 10 | 10 | 20 | 25 | 25 |
|  | 1.00 | PES | 100 | 80 | 50 | 50 | 50 | 100 | 70 | Z | 65 | 0 | 35 | 0 | 20 | 0 | 40 | 20 | 70 | 0 | 0 |
| 31 | 0.25 | PES | 0 | 0 | 0 | 0 | 0 | 0 | 0 | 0 | 0 | 0 | 0 | 0 | 0 | 0 | 0 | 40 | 0 | 0 | 10 |
|  | 0.50 | PES | 0 | 0 | 0 | 0 | 0 | 0 | 0 | 0 | 0 | 0 | 0 | 0 | 0 | 0 | 0 | 0 | 0 | 0 | 0 |
|  | 1.00 | PES | 0 | 10 | 20 | 0 | 0 | 0 | 10 | 20 | 15 | 25 | 25 | 0 | 50 | 0 | 0 | 20 | 25 | 25 | 0 |
| 32 | 0.25 | PES | 50 | 10 | 20 | 20 | 20 | 25 | 15 | 15 | 30 | 35 | 45 | 0 | 25 | 0 | 0 | 30 | 40 | 0 | 10 |
|  | 0.50 | PES | 85 | 15 | 80 | 30 | 30 | 50 | 25 | 25 | 30 | 40 | 0 | 0 | 30 | 0 | 0 | 0 | 40 | 0 | 15 |
|  | 0.50 | POS | 75 | 15 | 85 | 40 | 40 | 70 | 50 | 10 | 50 | 20 | 10 | 0 | 35 | 0 | 0 | 25 | 20 | 0 | 15 |
|  | 1.00 | POS | 0 | 0 | 0 | 0 | 0 | 0 | 100 | 0 | 70 | 75 | 10 | 0 | 15 | 0 | 0 | 25 | 90 | 0 | 30 |
| 33 | 0.25 | PES | 100 | 25 | 75 | 25 | 20 | 25 | 0 | 0 | 0 | 0 | 0 | 0 | 0 | 0 | 15 | 30 | 25 | 0 | 10 |
|  | 0.50 | PES | 100 | 25 | 80 | 30 | 30 | 50 | 15 | 0 | 0 | 35 | 0 | 0 | 0 | 0 | 0 | 0 | 25 | 0 | 10 |
|  | 1.00 | PES | 100 | 75 | 85 | 40 | 40 | 70 | 35 | 0 | 15 | 35 | 0 | 0 | 25 | 0 | 15 | 25 | 35 | 0 | 0 |
| 34 | 0.25 | PES | 25 | 0 | 0 | 0 | 0 | 0 | 0 | 0 | 0 | 0 | 0 | 0 | 0 | 0 | 0 | 0 | 0 | 0 | 0 |
|  | 0.50 | PES | 75 | 25 | 35 | 0 | 0 | 0 | 15 | 0 | 15 | 15 | 20 | 0 | 25 | 0 | 15 | 0 | 35 | 15 | 0 |
|  | 1.00 | PES | 100 | 10 | Z | Z | Z | 15 | 15 | 0 | 35 | 35 | 30 | 0 | 30 | 0 | 0 | 25 | 35 | 10 | 0 |
|  | 0.50 | POS | N | Z | Z | Z | 30 | 30 | 25 | 25 | 35 | 25 | 35 | 0 | 35 | 0 | 0 | 0 | 35 | 20 | 30 |
|  | 1.00 | POS | 0 | 0 | 0 | 0 | 0 | 0 | 30 | 35 | 40 | 40 | 0 | 0 | 0 | 0 | 0 | 0 | 0 | 0 | 20 |
| 35 | 0.25 | PES | 100 | 15 | 50 | 10 | 10 | 15 | 10 | 0 | 0 | 0 | 0 | 0 | 0 | 0 | 0 | 0 | 0 | 0 | 0 |
|  | 0.50 | PES | 100 | 35 | 65 | 25 | 15 | 30 | 15 | 0 | 25 | 15 | 10 | 0 | 25 | 0 | 0 | 0 | 10 | 0 | 0 |
|  | 1.00 | PES | 100 | 25 | 75 | 0 | 0 | 0 | 25 | 0 | 15 | 35 | 35 | 0 | 30 | 0 | 15 | 25 | 35 | 15 | 10 |
|  | 0.50 | POS | 0 | 0 | 0 | 15 | 25 | 0 | 20 | 25 | 40 | 25 | 45 | 0 | 0 | 0 | 0 | 0 | 30 | 10 | 30 |
|  | 1.00 | POS | 0 | 0 | 0 | 10 | 10 | 0 | 25 | 35 | 60 | 40 | 40 | 0 | 25 | 0 | 10 | 0 | 50 | 20 | 20 |
| 36 | 0.25 | PES | 35 | 0 | 60 | 30 | 25 | 35 | 75 | 0 | 0 | 0 | 0 | 0 | 0 | 0 | 0 | 25 | 0 | 0 | 0 |
|  | 0.50 | PES | 95 | 50 | 20 | 15 | 10 | 20 | 15 | 25 | 20 | 15 | 10 | 0 | 25 | 0 | 10 | 25 | 25 | 10 | 25 |
|  | 1.00 | PES | 50 | 50 | 35 | 30 | 30 | 15 | 20 | 35 | 35 | 35 | 35 | 0 | 15 | 0 | 15 | 0 | 25 | 15 | 25 |
|  | 1.00 | POS | 100 | 75 | 0 | 0 | 0 | 35 | 25 | 0 | 40 | 25 | 45 | 0 | 0 | 0 | 0 | 0 | 80 | 20 | 35 |
|  | 0.25 | PES | 0 | 0 | 0 | 0 | 0 | 0 | 15 | 10 | 25 | 50 | 60 | 0 | 15 | 0 | 15 | 0 | 20 | 0 | 35 |

TABLE III-continued

| Cmpd. No. | Rate lb/A | Method | FT | ARG | WG | SHC | WO | BSG | AMG | CB | SESB | VL | SP | YNS | SOY | WH | ML | RC | SB | CN | COT |
|---|---|---|---|---|---|---|---|---|---|---|---|---|---|---|---|---|---|---|---|---|---|
| 37 | 0.50 | POS | 0 | 0 | 0 | 0 | 0 | 0 | 20 | 20 | 40 | 35 | 35 | 0 | 30 | 0 | 0 | 0 | 35 | 25 | 35 |
|  | 1.00 | POS | 0 | 0 | 0 | 0 | 25 | 5 | 25 | 0 | 40 | 30 | 35 | 0 | 25 | 0 | 10 | 0 | 35 | 0 | 30 |
|  | 0.25 | PES | 90 | 10 | 5 | 0 | 5 | 5 | 0 | 0 | 5 | 10 | 0 | 0 | 5 | 0 | 5 | 0 | 80 | 0 | 5 |
|  | 0.50 | PES | 100 | 10 | 10 | 5 | 10 | 20 | 10 | 40 | 40 | 80 | 0 | 0 | 5 | 0 | 5 | 0 | 80 | 0 | 30 |
|  | 1.00 | PES | 100 | 40 | 30 | 10 | 20 | 40 | 10 | 50 | 60 | 80 | 0 | 0 | 10 | 0 | 0 | 0 | 100 | 5 | 30 |
|  | 0.25 | POS | 10 | 0 | 0 | 0 | 0 | 10 | 10 | 20 | 20 | 20 | 0 | 5 | 5 | 0 | 0 | 5 | 20 | 0 | 40 |
|  | 0.50 | POS | 50 | 10 | 0 | 0 | 20 | 40 | 10 | 20 | 40 | 20 | 0 | 0 | 10 | 0 | 0 | 5 | 90 | 5 | 40 |
|  | 1.00 | POS | 60 | 10 | 10 | 0 | 20 | 50 | 40 | 70 | 40 | 30 | 0 | N | 15 | 0 | 0 | 5 | 90 | 5 | 40 |
| 38 | 0.25 | PES | 100 | 15 | 50 | 35 | 0 | 0 | 10 | 0 | 20 | 20 | 10 | 0 | 0 | 25 | 0 | 25 | 35 | 30 | 25 |
|  | 0.50 | PES | 100 | 75 | 80 | 35 | 35 | 50 | 25 | 0 | 10 | 25 | 10 | 0 | 25 | 15 | 20 | 15 | 35 | 25 | 25 |
|  | 1.00 | PES | 100 | 20 | 80 | 0 | 35 | 50 | 35 | 0 | 35 | 30 | 15 | 0 | 30 | 30 | 20 | 30 | 100 | 30 | 40 |
| 39 | 0.50 | POS | 20 | 10 | 25 | 0 | 30 | 0 | N | N | N | N | N | 0 | 30 | 0 | 20 | 10 | 75 | 25 | 35 |
|  | 1.00 | POS | 20 | 30 | 35 | 50 | 20 | 0 | 35 | 35 | 75 | 75 | 70 | 10 | 30 | 0 | 20 | 0 | 40 | 20 | 35 |
|  | 2.00 | POS | 100 | 90 | 85 | 50 | 40 | 65 | 70 | 85 | 75 | 75 | 70 | 0 | 35 | 20 | 25 | 0 | 40 | 25 | 35 |
|  | 0.50 | PES | 100 | 90 | 85 | 50 | 50 | 80 | 75 | 35 | 50 | 60 | 65 | 0 | 60 | 25 | 30 | 10 | 100 | 20 | 60 |
|  | 1.00 | PES | 100 | 100 | 90 | 60 | 65 | 80 | 100 | 35 | 90 | 90 | 60 | 0 | 85 | 30 | 35 | 0 | 100 | 25 | 75 |
|  | 2.00 | PES | 100 | 100 | 90 | 60 | 65 | 80 | 100 | 80 | 100 | 100 | 100 | 0 | 85 | 30 | 40 | 0 | 100 | 25 | 85 |
| 40 | 0.25 | PES | 30 | 0 | 5 | 0 | 5 | 20 | 5 | N | 10 | 5 | 5 | 0 | 0 | 0 | 0 | 0 | 90 | 0 | 0 |
|  | 0.50 | PES | 100 | 10 | 10 | 5 | 0 | 20 | 20 | N | 10 | 5 | 10 | 0 | 5 | 0 | 0 | 0 | 90 | 0 | 0 |
|  | 1.00 | PES | 100 | 10 | 10 | 5 | 10 | 60 | 20 | N | 75 | 90 | 85 | 0 | 5 | 0 | 5 | 0 | 90 | 0 | 5 |
| 41 | 1.00 | PES | 100 | 5 | 5 | 5 | 5 | 5 | 30 | 50 | 30 | 20 | 0 | 0 | 10 | 0 | 0 | 5 | 100 | 0 | 5 |
| 42 | 0.25 | PES | 100 | 20 | 10 | 5 | 10 | 10 | 5 | 0 | 5 | 5 | 0 | 0 | 0 | 0 | 0 | 0 | 0 | 0 | 0 |
|  | 0.50 | PES | 100 | 40 | 40 | 10 | 20 | 20 | 10 | 10 | 80 | 75 | 0 | 0 | 0 | 5 | 5 | 0 | 50 | 5 | 5 |
| 43 | 0.50 | PES | 100 | 60 | 60 | 10 | 40 | 70 | 100 | 30 | 80 | 10 | 10 | 0 | 25 | 15 | 30 | 0 | 90 | 25 | 100 |
|  | 1.00 | PES | 90 | 70 | 75 | 35 | 35 | 90 | 80 | 20 | 95 | 75 | 65 | 25 | 35 | 15 | 35 | 15 | 95 | 40 | 85 |
|  | 2.00 | PES | 100 | 9 | 80 | 50 | 65 | 80 | 90 | 25 | 90 | 90 | 70 | 35 | 25 | 0 | 25 | 0 | 85 | 35 | 65 |
|  | 0.50 | POS | 100 | 100 | 85 | 50 | 30 | 0 | 50 | 40 | 95 | 95 | 75 | 30 | 40 | 0 | 0 | 0 | 50 | 20 | 35 |
|  | 1.00 | POS | 10 | 0 | 0 | 40 | 35 | 100 | 50 | 25 | 75 | 25 | 50 | 40 | 50 | 10 | 0 | 15 | 35 | 10 | 30 |
|  | 2.00 | POS | 10 | 0 | 10 | 30 | 35 | 30 | 40 | 50 | 75 | 35 | 50 | 0 | 35 | 25 | 0 | 20 | 50 | 35 | 25 |
| 44 | 0.25 | PES | 25 | 35 | 50 | 30 | 25 | 30 | 75 | 0 | 60 | 75 | 85 | 25 | 25 | 15 | 30 | 25 | 100 | 40 | 20 |
|  | 0.50 | PES | 100 | 50 | 95 | 40 | 50 | 50 | 80 | 30 | 95 | 100 | 20 | 20 | 40 | 0 | 35 | 15 | 100 | 35 | 20 |
|  | 1.00 | PES | 100 | 75 | 100 | 70 | 35 | 85 | 100 | 10 | 95 | 100 | 75 | 30 | 25 | 10 | 80 | 20 | 50 | 50 | 40 |
|  | 2.00 | PES | 100 | 100 | 100 | 75 | 40 | 95 | 100 | 30 | 100 | 100 | 20 | 40 | 50 | 25 | 80 | 20 | 100 | 65 | 25 |
|  | 0.25 | POS | 100 | 50 | 95 | 30 | 25 | 100 | 80 | 0 | 60 | 100 | 60 | 0 | 60 | 10 | 30 | 0 | 100 | 35 | 20 |
|  | 0.50 | POS | 100 | 75 | 100 | 40 | 50 | 85 | 100 | 0 | 95 | 100 | 20 | 0 | 25 | 0 | 35 | 25 | 100 | 40 | 30 |
|  | 1.00 | POS | 100 | 100 | 100 | 70 | 35 | 95 | 100 | N | 95 | 100 | 75 | 20 | 50 | 10 | 80 | 15 | 100 | 50 | 30 |
|  | 2.00 | POS | 100 | 75 | 100 | 75 | 40 | 100 | 100 | N | 100 | 100 | 85 | 40 | 60 | 25 | 80 | 25 | 100 | 65 | 40 |
| 45 | 1.00 | POS | 95 | 50 | 75 | 30 | 95 | 100 | 100 | N | 98 | 100 | 95 | 40 | 40 | 40 | 40 | 15 | 100 | 50 | 40 |
| 46 | 0.25 | PES | 100 | 95 | 100 | 80 | 50 | 80 | 100 | N | 100 | 100 | 20 | 0 | 5 | 5 | 25 | 0 | 50 | 10 | 5 |
|  | 0.50 | PES | 20 | 5 | 5 | 5 | 10 | 10 | 10 | 0 | 30 | 30 | 60 | 0 | 5 | 0 | 5 | 0 | 50 | 5 | 5 |
| 47 | 0.25 | PES | 95 | 10 | 5 | 5 | 10 | 40 | 5 | 0 | 0 | 80 | 100 | 0 | 5 | 0 | 5 | 0 | 90 | 5 | 30 |
|  | 0.50 | PES | 100 | 80 | 10 | 5 | 20 | 80 | 10 | 0 | 50 | 100 | 80 | 0 | 5 | 0 | 5 | 0 | 100 | 5 | 10 |
|  | 1.00 | PES | 100 | 80 | 10 | 30 | 30 | 85 | 10 | 5 | 60 | 100 | 60 | 0 | 10 | 10 | 5 | 0 | 90 | 5 | 100 |
|  | 0.50 | POS | 100 | 90 | 50 | 30 | 60 | 100 | 25 | 0 | 80 | 100 | 95 | 0 | 25 | 10 | 10 | 10 | 100 | 20 | 100 |
|  | 1.00 | POS | 100 | 95 | 70 | 40 | 40 | 40 | 75 | 5 | 90 | 95 | 95 | 0 | 15 | 10 | 10 | 0 | 100 | 5 | 100 |
| 48 | 0.25 | PES | 100 | 100 | 50 | 20 | 30 | 95 | 10 | 0 | 100 | 100 | 95 | 0 | 15 | 0 | 5 | 0 | 100 | 5 | 60 |

TABLE III-continued

| Cmpd. No. | Application Rate lb/A | Method | FT | ARG | WG | SHC | WO | BSG | AMG | CB | SESB | VL | SP | YNS | SOY | WH | ML | RC | SB | CN | COT |
|---|---|---|---|---|---|---|---|---|---|---|---|---|---|---|---|---|---|---|---|---|---|
|  | 0.50 | PES | 100 | 100 | 90 | 50 | 60 | 100 | 75 | 0 | 100 | 100 | 95 | 0 | 40 | 10 | 10 | 10 | 100 | 20 | 100 |
|  | 1.00 | PES | 100 | 100 | 100 | 90 | 90 | 100 | 100 | 5 | 100 | 100 | 100 | 0 | 50 | 20 | 40 | 10 | 100 | 10 | 90 |
|  | 0.25 | POS | 90 | 65 | 75 | 30 | 60 | 80 | 100 | N | 100 | 100 | 100 | 0 | 60 | 5 | 5 | 5 | 100 | 5 | 90 |
|  | 0.50 | POS | 100 | 80 | 95 | 40 | 100 | 100 | 100 | N | 100 | 100 | 100 | 0 | 60 | 20 | 20 | 30 | 100 | 20 | 90 |
| 49 | 1.00 | POS | 100 | 100 | 90 | 80 | 100 | 100 | 100 | 100 | 100 | 100 | 95 | 0 | 60 | 30 | 40 | 30 | 100 | 20 | 90 |
|  | 0.25 | PES | 100 | 95 | 80 | 40 | 20 | 80 | 10 | N | 40 | 30 | 30 | 0 | 100 | 0 | 10 | 0 | 90 | 5 | 5 |
|  | 0.50 | PES | 100 | 100 | 90 | 50 | 50 | 80 | 20 | 0 | 60 | 30 | 30 | 0 | 100 | 0 | 20 | 0 | 100 | 5 | 5 |
|  | 1.00 | PES | 100 | 100 | 95 | 50 | 70 | 80 | 50 | N | 80 | 30 | 30 | 0 | 30 | 10 | 30 | 0 | 100 | 5 | 10 |
|  | 0.25 | POS | 10 | 10 | 10 | 10 | 10 | 20 | 70 | 20 | 10 | 90 | 90 | 0 | 5 | 5 | 5 | 0 | 80 | 5 | 40 |
| 50 | 0.50 | PES | 95 | 30 | 5 | 5 | 10 | 40 | 10 | 0 | 0 | 60 | 30 | 0 | 5 | 0 | 5 | 0 | 40 | 0 | 5 |
|  | 0.25 | POS | 100 | 10 | 20 | 5 | 5 | 100 | 10 | 0 | 100 | 80 | 60 | 0 | 10 | 5 | 0 | 10 | 90 | 0 | 5 |
|  | 0.50 | POS | 10 | 60 | 10 | 10 | 5 | 5 | 5 | N | 90 | 60 | 80 | 0 | 10 | 5 | 5 | 0 | 100 | 5 | 50 |
| 51 | 0.25 | PES | 60 | 90 | 20 | 10 | 40 | 50 | 70 | 0 | 100 | 50 | 100 | 0 | 10 | 5 | 5 | 0 | 100 | 5 | 50 |
|  | 0.50 | PES | 100 | 95 | 80 | 40 | 60 | 70 | 10 | 0 | 40 | 30 | 30 | 0 | 5 | 5 | 5 | 10 | 100 | 5 | 50 |
|  | 1.00 | PES | 100 | 95 | 85 | 50 | 60 | 70 | 50 | 0 | 60 | 50 | 50 | 0 | 20 | 0 | 15 | 0 | 100 | 10 | 5 |
| 57 | 0.25 | PES | 100 | 100 | 95 | 70 | 80 | 80 | 50 | 0 | 60 | 80 | 95 | 0 | 20 | 5 | 20 | 0 | 100 | 5 | 5 |
|  | 0.50 | PES | 100 | 100 | 80 | 50 | 60 | 80 | 20 | 0 | 85 | 40 | 10 | 0 | 5 | 10 | 20 | 0 | 100 | 10 | 10 |
|  | 1.00 | PES | 100 | 100 | 90 | 60 | 75 | 80 | 60 | 5 | 95 | 95 | 60 | 0 | 10 | 5 | 30 | 0 | 100 | 10 | 10 |
|  | 1.00 | PES | 100 | 100 | 100 | 80 | 80 | 80 | 85 | 5 | 100 | 100 | 90 | 0 | 15 | 20 | 50 | 10 | 100 | 30 | 20 |

Test No. 3
Greenhouse Tests-Post-Emergence Post-Flood Application

This test illustrates the herbicidal activity of the various compounds listed below in the control of several broadleaf and grass weed species commonly associated with rice crops. The species tested were as follows:

| Common Name | Scientific Name | Abbreviation |
|---|---|---|
| Broadleaf Weeds: | | |
| annual morningglory | Ipomoea purpurea | AMG |
| hemp sesbania | Sesbania exaltata | SESB |
| Grasses: | | |
| yellow nutsedge | Cyperus esculentus | YNS |
| watergrass | Echinochloa crusgalli | WG |

The effect of the compounds on a rice crop (RC) grown adjacent to the weeds is also observed. Simulations of flood rice paddies were used for this test. The weed species and rice were planted simultaneously. Both direct seeded and transplanted rice were used to represent common growing techniques. The procedure was as follows:

Plastic tubs measuring 11.1 inches (28.2 cm) in depth, 6.7 inches (17.0 cm) in width, and 5.3 inches (13.5 cm) in depth were lined with plastic and filled to a depth of 2-3 inches (5.1-7.6 cm) with sandy loam soil containing 50 parts per million by weight (ppm) of cis-N-[(trichloromethyl)thio]4-cyclohexene-1,2-dicarboximide (a commercial fungicide known as "Captan") and 17-17-17 (percentages of $N-P_2O_5-K_2O$ on a weight basis) fertilizer.

On the 15th day after planting, the soil in each tube was flooded under 2-3 inches (5.1-7.6 cm) of water. The watergrass was in the two-leaf stage by this time and was completely submerged by the water. The other weed species and the rice were all at the water line or slightly above. The test compounds were then added on the next day to the flood water from stock solutions made by dissolving 88 mg of test compound in 40 ml acetone containing 0.1% (by weight) of a polyoxyethylene sorbitan monolaurate surface-active agent. Aliquots of the appropriate amount of solution were used to provide an application rate ranging from 0.13 to 2.0 pounds of active ingredient per acre (0.14 to 2.24 kilograms per hectare) in equivalent terms.

The water level was then maintained in each tub for three weeks, at which time each species was evaluated for percent injury. The evaluation was a visual rating comparing the treated plants to untreated plants grown under otherwise identical conditions in a separate tub. The ratings ranged from 0 to 100%, with 0 representing no injury and 100% representing complete kill. The injury ratings represented total plant injury due to all factors. The results are shown in Table IV.

TABLE IV

| Compound No. | Application rate (lb/A) | Rice Screen - Post-Flood Application Percent Injury | | | | |
|---|---|---|---|---|---|---|
| | | WG | AMG | SESB | YNS | RC |
| 2 | 0.50 | 65 | 80 | 0 | 20 | 25 |
| | 1.00 | 75 | 90 | 30 | 25 | 50 |
| | 2.00 | 80 | 100 | 20 | 25 | 45 |
| 6 | 0.25 | 100 | 100 | 100 | 0 | 20 |
| | 0.50 | 100 | 100 | 100 | 30 | 30 |
| | 1.00 | 100 | 100 | 100 | 30 | 75 |
| 7 | 1.00 | 25 | 90 | 90 | 0 | 0 |
| 8 | 0.50 | 100 | 100 | 100 | 20 | 60 |
| | 1.00 | 100 | 100 | 100 | 20 | 100 |

TABLE IV-continued

| Compound No. | Application rate (lb/A) | Rice Screen - Post-Flood Application Percent Injury | | | | |
|---|---|---|---|---|---|---|
| | | WG | AMG | SESB | YNS | RC |
| 10 | 0.25 | 70 | 100 | 100 | 0 | 0 |
| | 0.50 | 95 | 100 | 100 | 0 | 0 |
| | 1.00 | 100 | 100 | 100 | 0 | 10 |
| | 2.00 | 100 | 100 | 100 | 0 | 25 |
| 12 | 0.13 | 100 | 60 | 50 | 0 | 20 |
| | 0.25 | 100 | 80 | 80 | 20 | 40 |
| | 0.50 | 100 | 40 | 50 | 15 | 50 |
| | 1.00 | 100 | 100 | 100 | 25 | 40 |
| | 2.00 | 100 | 100 | 100 | 25 | 60 |
| 14 | 0.25 | 95 | 100 | 100 | 0 | 10 |
| | 0.50 | 100 | 100 | 100 | 0 | 20 |
| | 1.00 | 100 | 100 | 100 | 0 | 20 |
| 16 | 0.25 | 80 | 100 | 100 | 0 | 0 |
| | 0.50 | 90 | 100 | 100 | 0 | 25 |
| | 1.00 | 100 | 100 | 100 | 0 | 80 |
| 19 | 0.25 | 50 | 100 | 100 | N | 0 |
| | 0.50 | 50 | 100 | 100 | N | 0 |
| | 1.00 | 90 | 100 | 100 | 0 | 0 |
| 21 | 1.00 | 0 | 0 | 0 | 0 | 0 |
| | 2.00 | 30 | 0 | 0 | 0 | 0 |
| 22 | 1.00 | 85 | 0 | 0 | N | 20 |
| | 2.00 | 85 | 0 | 0 | N | 10 |
| 24 | 1.00 | 85 | 75 | 60 | 75 | 65 |
| | 2.00 | 1000 | 85 | 100 | 85 | 80 |
| 25 | 1.00 | 25 | 70 | 20 | 0 | 0 |
| | 2.00 | 40 | 60 | 20 | 0 | 20 |
| 27 | 1.00 | 65 | 0 | 0 | 0 | 25 |
| | 2.00 | 70 | 0 | 0 | 0 | 40 |
| 28 | 1.00 | 40 | 0 | 0 | 0 | 0 |
| | 2.00 | 50 | 0 | 0 | 0 | 25 |
| 30 | 0.50 | 75 | 0 | 0 | N | 0 |
| | 1.00 | 95 | 0 | 20 | N | 0 |
| | 2.00 | 95 | 20 | 40 | N | 20 |
| 38 | 1.00 | 80 | 60 | 30 | 0 | 25 |
| | 2.00 | 80 | 90 | 20 | 0 | 35 |
| 40 | 1.00 | 30 | 100 | 80 | 0 | 10 |
| 42 | 1.00 | 40 | 40 | 10 | 0 | 0 |
| | 2.00 | 40 | 50 | 20 | 0 | 0 |
| 45 | 0.25 | 80 | 20 | 100 | 0 | 0 |
| | 0.50 | 95 | 100 | 100 | 25 | 10 |
| | 1.00 | 85 | 100 | 100 | 10 | 10 |
| 46 | 0.25 | 65 | 20 | 0 | 0 | 0 |
| | 0.50 | 50 | 20 | 30 | 0 | 0 |
| | 1.00 | 65 | 40 | 0 | 0 | 0 |
| 47 | 0.25 | 70 | 30 | 0 | 0 | 20 |
| | 0.50 | 70 | 100 | 50 | 0 | 30 |
| | 1.00 | 100 | 100 | 40 | 0 | 25 |
| 48 | 0.25 | .85 | 100 | 100 | 0 | 10 |
| | 0.50 | 100 | 100 | 100 | 0 | 10 |
| | 1.00 | 100 | 100 | 100 | 20 | 25 |
| 50 | 1.00 | 60 | 20 | 100 | 0 | 0 |
| 57 | 0.25 | 100 | 60 | 60 | 0 | 20 |
| | 0.50 | 90 | 100 | 100 | 0 | 40 |
| | 1.00 | 100 | 100 | 100 | 0 | 50 |

Test No. 4

Still another series of tests were conducted against a series of weed species commonly found in Europe. These weed species were as follows:

| Common Name | Scientific Name | Abbreviation |
|---|---|---|
| blackgrass | Alopecurus myosuroides | BKGR |
| perennial ryegrass | Lolium perrenne | PRGR |
| wild oat | Avena fatua | WO |
| poverty brome | Bromus sterilis | PBRO |
| scented mayweed | Matricaria recutita | MARE |
| common chickweed | Stellaria media | CCHW |
| ivyleaf speedwell | Veronica hederifolis | ILSW |
| mustard | Sinapis arvensis | MD |
| annual bluegrass | Poa annua | ABG |
| carrot | Daucus catora | CARO |
| catchweed bedstraw | Galium aparine | BDSW |

Also included in this series of tests were various crop species as follows:

| sugarbeet - Amazon | Beta vulgaris | SB |
|---|---|---|
| barley | Hordeum vulgare | BA |
| wheat | Triticum aestivum | WH |

Aluminum loaf pans measuring 19×8×6 cm were filled with loamy sand soil amended with 75 ppm Captan fungicide. Six furrows were made across the width of the pan. Seeds were placed in the furrows and then covered with soil. Some species, namely *Matricaria recutita* and *Stellaria media* were sown on the soil surface to ensure adequate germination and establishment. Two loaf pans were used for each treatment for a total of 12 plant species. Three of the 12 plant species were crops: sugarbeets, winter barley and winter wheat. Remaining species were monocot and dicot weeds associated with those crops.

Flats to be treated with a pre-emergence spray treatment were immediately treated with seeding, and before watering of the flats. Flats to be treated with a post-emergence spray treatment were kept in the greenhouse and grown until ready for treatment. Dicots had the first true leaf tissue expanded, and monocots had one to two leaves at the time of treatment.

Chemicals were weighed into 60 ml clear bottles using a Sartorius scale. The amount of chemical needed was determined from the following information:

| Carrier Volume (gallons/acre) | mg Chemical/ml Solvent |
|---|---|
| 20 | 6.0 = 1.0 pound active ingredient/acre |
| 25 | 4.8 = 1.0 pound active ingredient/acre |
| 30 | 4.0 = 1.0 pound active ingredient/acre |
| 40 | 3.0 = 1.0 pound active ingredient/acre |
| 50 | 2.4 = 1.0 pound active ingredient/acre |
| 80 | 1.5 = 1.0 pound active ingredient/acre |

Forty gallons/acre was the carrier volume and unless otherwise stated.

A 1:1 ratio of acetone/water was used to solve technical grade compounds to form a spray solution. Polyoxyethylene sorbitan monlaurate (Tween ®20) was added to the acetone at a concentration of 1%. The chemicals were first solved in this mixture before addition of the water. The total solution volume for each treatment was 40 ml. Only water was used to put formulated materials into solution.

Spray solutions were delivered to the soil surface or foliage by use of a linear spray table operated at 30 PSI. Flats were immediately placed in the greenhouse after spraying. Pre-emergence treated flats were watered from overhead. Foliage of post-emergence treatments was not dosed with water so as to maintain placement of the chemical.

Greenhouse air temperatures ranged from 15° C. to 24° C. during the year. Whitewash was maintained on the glazing all year in order to reduce light intensities as much as possible. A cool and shady greenhouse environment helps to simulate the field environment in which these crops and weeds grow.

Three to four weeks after treatment, each row of seedlings or plants was visually rated for growth, injury or control due to all facts of herbicide or chemical affect. Symptomologies were recorded for each compound showing activity. Untreated flats were used for comparison, and their growth was considered as 0% injury. One hundred percent injury was equivalent to complete kill.

The results are shown in Table V.

TABLE V

| Cmpd. No. | Application Rate (lb/A) | Method | BKGR | PRGR | WO | PBRO | MARE | CCHW | BDSW | ILSW | MD | SB | BA | WH |
|---|---|---|---|---|---|---|---|---|---|---|---|---|---|---|
| 1 | 2.00 | PES | 40 | 35 | 50 | 20 | 70 | 75 | 30 | N | 35 | 100 | 0 | 0 |
|  | 2.00 | POS | 15 | 0 | 40 | 0 | 20 | 90 | N | 100 | 90 | 100 | 0 | 14 |
| 3 | 0.25 | POS | 85 | 45 | 60 | 20 | 90 | 100 | 70 | N | 100 | 100 | 15 | 20 |
|  | 0.50 | POS | 90 | 50 | 65 | 35 | 90 | 100 | 55 | N | 100 | 100 | 20 | 25 |
|  | 1.00 | POS | 100 | 70 | 65 | 55 | 95 | 100 | 65 | N | 100 | 100 | 20 | 20 |
|  | 2.00 | POS | 100 | 90 | 90 | 90 | 100 | 100 | 70 | N | 100 | 100 | 20 | 20 |
| 4 | 2.00 | PES | 75 | 35 | 20 | 15 | 0 | 0 | 15 | N | 25 | 100 | 0 | 0 |
|  | 2.00 | POS | 35 | 0 | 0 | 0 | 20 | 90 | N | 100 | 90 | 100 | 0 | 0 |
|  | 0.50 | PES | 90 | 80 | 65 | 30 | 100 | 100 | 25 | N | 100 | 100 | 40 | 20 |
|  | 1.00 | PES | 95 | 95 | 75 | 40 | 100 | 100 | 20 | N | 100 | 100 | 45 | 25 |
| 5 | 0.50 | POS | 100 | 100 | 90 | 60 | 100 | 90 | 100 | 100 | 100 | 100 | 50 | 45 |
|  | 1.00 | POS | 100 | 100 | 95 | 80 | 100 | 100 | 100 | 100 | 100 | 100 | 55 | 65 |
| 6 | 0.25 | PES | 97 | 70 | 85 | N | 0 | 45 | 70 | N | 30 | 40 | 30 | 20 |
|  | 0.50 | PES | 100 | 80 | 90 | N | 75 | 20 | 60 | N | 35 | 65 | 50 | 40 |
|  | 1.00 | PES | 100 | 95 | 80 | N | 80 | 90 | 30 | N | 50 | 100 | 70 | 75 |
|  | 2.00 | PES | 100 | 95 | 90 | N | 70 | 90 | 40 | N | 90 | 100 | 80 | 80 |
|  | 0.25 | POS | 50 | 80 | 80 | N | 50 | N | 40 | N | 100 | 100 | 65 | 60 |
|  | 0.50 | POS | 55 | 70 | 90 | N | 50 | 50 | 45 | N | 100 | 100 | 70 | 65 |
|  | 1.00 | POS | 60 | 90 | 100 | N | 60 | 60 | 45 | N | 100 | 100 | 70 | 75 |
|  | 2.00 | POS | 70 | 100 | 100 | N | 65 | 70 | 50 | N | 100 | 100 | 75 | 70 |
| 7 | 0.25 | PES | 95 | 80 | 70 | 40 | 0 | 0 | 15 | N | 20 | 20 | 20 | 15 |
|  | 0.50 | PES | 100 | 95 | 90 | 75 | 0 | 0 | 25 | N | 30 | 35 | 40 | 30 |
|  | 1.00 | PES | 100 | 100 | 95 | 90 | 40 | 30 | 40 | N | 45 | 40 | 55 | 45 |
|  | 2.00 | PES | 100 | 100 | 100 | 100 | 55 | 40 | 45 | N | 50 | 100 | 85 | 90 |
| 8 | 1.00 | PES | 100 | 90 | 90 | N | 60 | 10 | 35 | N | 45 | 100 | 80 | 75 |
|  | 0.25 | POS | 70 | 70 | 90 | N | 60 | 40 | 60 | N | 65 | 65 | 70 | 70 |
|  | 0.50 | POS | N | 100 | 100 | N | 90 | 90 | 90 | N | 75 | 95 | 80 | 80 |
|  | 1.00 | POS | 75 | 100 | 100 | N | 90 | 90 | 70 | N | 70 | 100 | 80 | 85 |
|  | 2.00 | POS | 70 | 100 | 100 | N | 90 | 40 | 85 | N | 60 | 100 | 80 | 85 |
| 9 | 0.25 | PES | 100 | 100 | 70 | 40 | 75 | 90 | 20 | N | 100 | 75 | 10 | 15 |
|  | 0.50 | PES | 100 | 100 | 90 | 60 | 80 | 100 | 25 | 60 | 100 | 100 | 15 | 20 |

TABLE V-continued

| Cmpd. No. | Rate (lb/A) | Application Method | BKGR | PRGR | WO | PBRO | MARE | CCHW | BDSW | ILSW | MD | SB | BA | WH |
|---|---|---|---|---|---|---|---|---|---|---|---|---|---|---|
| | 1.00 | PES | 100 | 100 | 100 | 100 | 100 | 100 | 40 | 100 | 100 | 100 | 20 | 15 |
| | 2.00 | PES | 100 | 100 | 100 | 100 | 80 | 100 | 45 | 100 | 100 | 100 | 25 | 25 |
| | 0.25 | POS | 50 | 90 | 90 | 40 | 75 | 100 | 50 | 80 | 90 | 100 | N | 10 |
| | 0.50 | POS | 100 | 100 | 100 | 85 | 100 | 100 | 90 | 100 | 100 | 100 | N | 40 |
| | 1.00 | POS | 100 | 100 | 95 | 100 | 100 | 100 | 100 | 100 | 100 | 100 | N | 100 |
| | 2.00 | POS | 100 | 100 | 95 | 90 | 90 | 100 | 70 | 100 | 100 | 100 | N | 55 |
| 10 | 2.00 | PES | 95 | 90 | 80 | 65 | 100 | N | 50 | N | 100 | 100 | 55 | 45 |
| 12 | 2.00 | PES | 100 | 95 | 70 | 80 | 95 | 20 | 35 | N | 45 | 100 | 65 | 60 |
| | 2.00 | POS | 80 | 70 | 80 | 70 | 20 | 20 | 40 | N | 80 | 75 | 70 | 65 |
| 13 | 2.00 | PES | 100 | 100 | 95 | 90 | 100 | 100 | 65 | 100 | 100 | 100 | 70 | 75 |
| | 2.00 | POS | 90 | 75 | 100 | 85 | N | 65 | 50 | 100 | 100 | 100 | 0 | 20 |
| 14 | 2.00 | PES | 95 | 80 | 75 | 40 | 0 | 0 | 15 | N | 35 | 20 | 15 | 20 |
| | 2.00 | POS | 75 | 55 | 70 | 40 | 80 | 30 | 45 | N | 90 | 55 | 45 | 25 |
| | 0.25 | PES | 50 | 30 | 15 | N | 0 | 0 | 0 | N | 35 | 0 | 0 | 0 |
| | 0.50 | PES | 55 | 50 | 25 | N | 0 | 0 | 0 | N | 5 | 0 | 0 | 0 |
| | 1.00 | PES | 60 | 55 | 55 | N | 0 | 0 | 20 | N | 100 | 35 | 20 | 10 |
| | 2.00 | PES | 70 | 70 | 60 | N | 0 | 20 | 30 | N | 100 | 60 | 25 | 15 |
| 15 | 2.00 | PES | 100 | 100 | 90 | 85 | 100 | 100 | 60 | N | 100 | 100 | 20 | 40 |
| | 2.00 | PES | 85 | 80 | 90 | 85 | 100 | 65 | 55 | N | 100 | 100 | 40 | 30 |
| 16 | 0.25 | PES | 95 | 50 | 70 | N | 0 | 20 | 20 | N | 20 | 30 | 20 | 10 |
| | 0.50 | PES | 100 | 70 | 80 | N | 0 | 25 | 25 | N | 30 | 50 | 40 | 20 |
| | 1.00 | PES | 100 | 100 | 85 | N | 15 | 40 | 30 | N | 35 | 70 | 50 | 60 |
| | 2.00 | PES | 100 | 100 | 95 | N | 70 | 70 | 40 | N | 45 | 95 | 60 | 65 |
| | 2.00 | POS | 70 | 65 | 70 | 85 | 55 | 50 | 50 | N | 60 | 100 | 65 | 50 |
| 17 | 2.00 | POS | 60 | 65 | 80 | 60 | 70 | 50 | 50 | N | 100 | 100 | 20 | 0 |
| 18 | 2.00 | PES | 100 | 90 | 75 | 60 | 90 | 30 | 20 | N | 95 | 65 | 20 | 25 |
| | 2.00 | POS | 55 | 40 | 70 | 30 | 100 | 50 | 50 | N | N | 100 | 20 | 15 |
| 19 | 0.25 | PES | 90 | 40 | 50 | 20 | 0 | 20 | 20 | N | 30 | 15 | 20 | 0 |
| | 0.50 | PES | 100 | 50 | 70 | 25 | 15 | 25 | 30 | N | 30 | 20 | 25 | 20 |
| | 1.00 | PES | 100 | 85 | 90 | 50 | 25 | 30 | 35 | N | 40 | 40 | 30 | 35 |
| | 2.00 | PES | 100 | 90 | 90 | 75 | 30 | 40 | 35 | N | 45 | 100 | 40 | 45 |
| 24 | 2.00 | PES | 95 | 90 | 80 | 60 | 55 | N | 45 | N | 45 | 90 | 45 | 35 |
| 31 | 2.00 | PES | 45 | 10 | 15 | 0 | 0 | 0 | 0 | N | 80 | 20 | 0 | 0 |
| | 2.00 | POS | 20 | 15 | 30 | 0 | 30 | 35 | 40 | N | 40 | 80 | 10 | 15 |
| 32 | 2.00 | PES | 85 | 65 | 20 | 20 | 55 | 40 | 20 | N | 30 | 85 | 0 | 0 |
| | 2.00 | POS | 50 | 20 | 30 | 30 | 20 | 50 | N | 100 | 100 | 100 | 0 | 20 |
| 33 | 0.25 | PES | 95 | 50 | 60 | N | 0 | 20 | 20 | N | 40 | 65 | 0 | 0 |
| | 0.50 | PES | 100 | 60 | 65 | N | 0 | 50 | 25 | N | 45 | 65 | 0 | 10 |
| | 1.00 | PES | 100 | 65 | 70 | N | 0 | 30 | 20 | N | 45 | 45 | 10 | 15 |
| | 2.00 | PES | 100 | 65 | 60 | N | 15 | N | 30 | N | 50 | 50 | 15 | 15 |
| | 0.25 | POS | 40 | 60 | 70 | N | 50 | 60 | 30 | N | 90 | 90 | 40 | 30 |
| | 0.50 | POS | 50 | 60 | 75 | N | 55 | 50 | 40 | N | 95 | 90 | 55 | 35 |
| | 1.00 | POS | 55 | 60 | 80 | N | 60 | 55 | 45 | N | 95 | 90 | 50 | 40 |
| | 2.00 | POS | 50 | 50 | 85 | N | 60 | 55 | 45 | N | 100 | 90 | 55 | 40 |
| 34 | 2.00 | POS | 75 | 45 | 55 | 30 | 40 | 100 | N | 100 | 100 | 100 | 30 | 35 |
| | 0.25 | PES | 0 | 0 | 0 | 0 | 0 | 0 | 0 | N | 80 | 0 | 0 | 0 |
| | 0.50 | PES | 0 | 0 | 0 | 0 | 0 | 0 | 0 | N | 100 | 0 | 0 | 0 |
| | 2.00 | PES | 100 | 100 | 60 | 50 | 95 | 100 | 50 | N | 100 | 0 | 0 | 0 |
| 35 | 0.25 | PES | 95 | 45 | 40 | 0 | 0 | 0 | 0 | N | 70 | 60 | 0 | 0 |
| | 0.50 | PES | 95 | 55 | 45 | 0 | 0 | 0 | 0 | N | 80 | 15 | 0 | 0 |
| | 1.00 | PES | 95 | 60 | 55 | 10 | 0 | 0 | 0 | N | 80 | 20 | 0 | 0 |
| | 2.00 | PES | 95 | 70 | 55 | 20 | 20 | 30 | 35 | N | 90 | 15 | 0 | 0 |
| | 0.25 | POS | 30 | 0 | 30 | 0 | N | 95 | 35 | N | 100 | 100 | 0 | 0 |
| | 0.50 | POS | 60 | 20 | 40 | 0 | 40 | 100 | 45 | N | 100 | 100 | 0 | 15 |
| | 1.00 | POS | 90 | 30 | 45 | 20 | 50 | 100 | 50 | N | 100 | 100 | 0 | 20 |
| | 2.00 | POS | 95 | 45 | 60 | 30 | 90 | 100 | 55 | N | 100 | 100 | 10 | 20 |
| 36 | 2.00 | PES | 100 | 100 | 65 | 45 | 95 | 95 | 45 | N | 100 | 100 | 20 | 15 |
| | 2.00 | POS | 90 | 35 | 40 | 35 | 20 | 100 | N | 100 | 100 | 100 | 30 | 35 |
| | 0.25 | PES | 90 | 50 | 40 | 15 | 100 | 50 | 20 | N | 100 | 100 | 0 | 0 |
| | 0.50 | PES | 90 | 55 | 60 | 20 | 85 | 50 | 15 | N | 100 | 80 | 0 | 0 |
| | 1.00 | PES | 95 | 65 | 70 | 15 | 85 | 45 | 30 | N | 100 | 80 | 0 | 0 |
| 37 | 2.00 | PES | 100 | 100 | 80 | 65 | 20 | 40 | 40 | N | 70 | 75 | 60 | 65 |
| | 2.00 | POS | 70 | 80 | 80 | 40 | 80 | 95 | 45 | N | 100 | 100 | 50 | 35 |
| 38 | 2.00 | PES | 100 | 100 | 65 | 45 | 100 | 100 | 40 | 85 | 100 | 100 | 30 | 45 |
| | 0.25 | PES | 55 | 45 | 20 | 0 | 0 | 0 | 0 | N | 70 | 0 | 0 | 0 |
| | 0.50 | PES | 85 | 50 | 55 | 15 | 50 | 70 | 20 | N | N | 40 | 0 | 0 |
| | 1.00 | PES | 90 | 85 | 60 | 40 | 90 | 75 | 45 | N | 100 | 55 | 0 | 0 |
| | 2.00 | PES | 100 | 80 | 65 | 45 | 40 | 70 | 40 | N | N | 90 | 0 | 0 |
| | 0.25 | PES | 85 | 70 | 80 | N | 15 | 20 | 0 | N | 20 | 40 | 30 | 20 |
| | 0.50 | PES | 90 | 70 | 80 | N | 10 | 30 | 20 | N | 25 | 45 | 25 | 20 |
| | 1.00 | PES | 100 | 75 | 85 | N | 15 | 50 | 25 | N | 55 | 60 | 30 | 25 |
| | 2.00 | PES | N | N | N | N | N | N | N | N | N | N | N | N |
| | 0.25 | POS | 30 | 70 | 80 | N | 65 | 50 | 40 | N | 100 | 100 | 60 | 60 |
| | 0.50 | POS | 40 | 80 | 80 | N | 65 | 50 | 45 | N | 100 | 100 | 50 | N |
| | 1.00 | POS | 50 | 70 | 100 | N | 60 | 60 | 50 | N | 100 | 100 | 60 | N |
| | 2.00 | POS | N | N | N | N | N | N | N | N | N | N | N | N |
| 39 | 2.00 | PES | 100 | 100 | 75 | 55 | 100 | 100 | 55 | 50 | 100 | 100 | 60 | 65 |
| | 2.00 | POS | 90 | 100 | 95 | 50 | 60 | 100 | 85 | 100 | 100 | 100 | N | 45 |
| | 0.25 | PES | 100 | 90 | 55 | 20 | 90 | 50 | 40 | N | 100 | 100 | 20 | 10 |

TABLE V-continued

| Cmpd. No. | Application Rate (lb/A) | Method | BKGR | PRGR | WO | PBRO | MARE | CCHW | BDSW | ILSW | MD | SB | BA | WH |
|---|---|---|---|---|---|---|---|---|---|---|---|---|---|---|
| | 0.50 | PES | 100 | 100 | 70 | 35 | 95 | 60 | 50 | N | 90 | 100 | 35 | 20 |
| | 1.00 | PES | 100 | 100 | 70 | 60 | 100 | 70 | 55 | N | 100 | 100 | 60 | 40 |
| | 2.00 | PES | 100 | 100 | 85 | 65 | 100 | 95 | 70 | N | 100 | 100 | 70 | 65 |
| | 0.25 | POS | 80 | 70 | 45 | 20 | 90 | 95 | 45 | N | 100 | 100 | 30 | 20 |
| | 0.50 | POS | 90 | 100 | 70 | 50 | 100 | 100 | 60 | N | 100 | 100 | 70 | 60 |
| | 2.00 | POS | 95 | 100 | 90 | 80 | 100 | 100 | 65 | N | 100 | 100 | 70 | 60 |
| 40 | 2.00 | PES | 15 | 30 | 45 | 20 | 0 | 0 | 0 | N | 0 | 15 | 20 | 0 |
| | 2.00 | POS | 45 | 55 | 60 | 0 | 90 | 30 | 40 | N | 100 | 100 | 0 | 0 |
| 41 | 2.00 | PES | 100 | 85 | 90 | 40 | 0 | 0 | 20 | N | 35 | 40 | 30 | 20 |
| | 0.25 | PES | 25 | 30 | 20 | N | 15 | 10 | 20 | N | 20 | 20 | 0 | 0 |
| | 0.50 | PES | 45 | 40 | 40 | N | 20 | 40 | 20 | N | 30 | 70 | 20 | 10 |
| | 1.00 | PES | 90 | 50 | 45 | N | 15 | 20 | 25 | N | 35 | 40 | 20 | 10 |
| | 2.00 | PES | 95 | 60 | 50 | N | 15 | 60 | 30 | N | 40 | 80 | 25 | 10 |
| 42 | 2.00 | PES | 100 | 80 | 85 | 45 | 0 | 0 | 30 | N | 55 | 60 | 30 | 20 |
| 45 | 2.00 | PES | 95 | 80 | 70 | N | 20 | 35 | 20 | N | 70 | 80 | 20 | 15 |
| 46 | 0.25 | PES | 40 | 25 | 0 | N | 70 | 0 | 20 | N | 35 | 15 | 0 | 0 |
| | 0.50 | PES | 70 | 45 | 35 | N | 80 | 20 | 30 | N | 35 | 40 | 0 | 0 |
| | 1.00 | PES | 95 | 60 | 45 | N | 65 | 30 | 40 | N | 40 | 45 | 0 | 0 |
| | 2.00 | PES | 100 | 65 | 80 | N | 70 | 30 | 45 | N | 40 | N | 25 | 20 |
| 47 | 0.25 | PES | 75 | 70 | 60 | N | 70 | 20 | 20 | N | 80 | 85 | 20 | 15 |
| | 0.50 | PES | 95 | 90 | 75 | N | 95 | 55 | 30 | N | 80 | 100 | 25 | 20 |
| | 1.00 | PES | 100 | 100 | 90 | N | 95 | 50 | 35 | N | 35 | 100 | 30 | 25 |
| | 2.00 | PES | 100 | 100 | 80 | N | 100 | 50 | 35 | N | 85 | 100 | 35 | 20 |
| | 0.25 | POS | 40 | 100 | 100 | N | 30 | 40 | 30 | N | 100 | 90 | 40 | 30 |
| | 0.50 | POS | 55 | 100 | 100 | N | 40 | 70 | 40 | N | 100 | 100 | 45 | 35 |
| | 1.00 | POS | 60 | 100 | 100 | N | 45 | 75 | 50 | N | 100 | 100 | 50 | 40 |
| | 2.00 | POS | 65 | 100 | 100 | N | 50 | 70 | 55 | N | 100 | 100 | 60 | 50 |
| | 2.00 | PES | 100 | 100 | 80 | N | 55 | 60 | 35 | N | 45 | 100 | 70 | 70 |
| | 2.00 | POS | 100 | 100 | 80 | N | 55 | 80 | 35 | N | 45 | 100 | | |
| 48 | 2.00 | PES | 100 | 100 | 100 | N | 95 | 100 | 55 | N | 100 | 100 | 90 | 90 |
| | 2.00 | POS | 50 | 90 | 85 | N | 40 | 80 | 55 | N | 95 | 100 | 85 | 80 |
| 49 | 2.00 | PES | 100 | 75 | 70 | N | 100 | 90 | 30 | N | 75 | 100 | 40 | 25 |
| | 2.00 | POS | 90 | 70 | 50 | N | 30 | 100 | 40 | N | 95 | 100 | 45 | 35 |
| 50 | 2.00 | PES | 95 | 70 | 30 | N | 30 | 50 | 30 | N | 90 | 95 | 20 | 0 |
| | 2.00 | POS | 35 | 60 | 65 | N | 30 | 85 | 40 | N | 90 | 100 | 35 | 20 |
| 51 | 2.00 | PES | 100 | 100 | 80 | N | 100 | 90 | 40 | N | 80 | 100 | 40 | 20 |
| | 2.00 | POS | 50 | 45 | 40 | N | 40 | 100 | 40 | N | 75 | 100 | 0 | 0 |
| 57 | 2.00 | PES | 95 | 80 | 70 | N | 65 | 40 | 45 | N | 85 | 100 | 60 | 60 |

METHODS OF APPLICATION

The herbicidal compositions of the present invention are useful in controlling the growth of undesirable vegetation by pre-emergence or post-emergence application to the locus where control is desired, including pre-plant and post-plant soil incorporation as well as surface application. The compositions are generally embodied in formulations suitable for convenient application. Typical formulations contain additional ingredients or diluent carriers which are either inert or active. Examples of such ingredients or carriers are water, organic solvents, dust carriers, granular carriers, surface active agents, oil and water, water-oil emulsions, wetting agents, dispersing agents, and emulsifying agents. The herbicidal formulations generally take the form of dusts, emulsifiable concentrates, granules and pellets, or microcapsules.

A. DUSTS

Dusts are dense powder compositions which are intended for application in dry form. Dusts are characterized by their free-flowing and rapid settling properties so that they are not readily windborne to areas where their presence is not desired. They contain primarily an active material and a dense, free-flowing, solid carrier.

Their performance is sometimes aided by the inclusion of a wetting agent, and convenience in manufacture frequently demands the inclusion of an inert, absorptive grinding aid. For the dust compositions of this invention, the inert carrier may be either of vegetable or mineral origin, the wetting agent is preferably anionic or nonionic, and suitable absorptive grinding aids are of mineral origin.

Suitable classes of inert solid carriers for use in the dust compositions are those organic or inorganic powders which possess high bulk density and are very free-flowing. They are also characterized by low surface area and poor liquid absorptivity. Suitable grinding aids are natural clays, diatomaceous earths, and synthetic mineral fillers derived from silica or silicate. Among ionic and nonionic wetting agents, the most suitable are the members of the group kown to the art as wetting agents and emulsifiers. Although solid agents are preferred because of ease of incorporation, some liquid nonionic agents are also suitable in the dust formulations.

Preferred dust carriers are micaceous talcs, pyrophyllite, dense kaolin clays, tobacco dust and ground calcium phosphate rock.

Preferred grinding aids are attapulgite clay, diatomaceous silica, synthetic fine silica and synthetic calcium and magnesium silicates.

Most preferred wetting agents are alkylbenzene and alkyl-naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Preferred dispersants are methyl cellulose, polyvinyl alcohol, lignin sulfonates, polymeric alkylnaphthalene sulfonates, sodium naphthalenesulfonate, polymethylene bisnaphthalenesulfonate, and sodium-N-methyl-N-(long chain acid) taurates.

The inert solid carriers in the dusts of this invention are usually present in concentrations of from about 30 to 90 weight percent of the total composition. The grinding aid will usually constitute 5 to 50 weight percent of the compositions, and the wetting agent will constitute from about 0 to 1.0 weight percent of the composition. Dust compositions can also contain other surfactants such as dispersing agents in concentrations of up to about 0.5 weight percent, and minor amounts of anticaking and antistatic agents. The particle size of the carrier is usually in the range of 30 to 50 microns.

B. EMULSIFIABLE CONCENTRATES

Emulsifiable concentrates are usually solutions of the active materials in nonwater-miscible solvents together with an emulsifying agent. Prior to use, the concentrate is diluted with water to form a suspended emulsion of solvent droplets.

Typical emulsifying agents are anionic or nonionic surfactants, or mixtures of the two. Examples include long-chain alkyl or mercaptan polyethoxy alcohols, alkylaryl polyethoxy alcohols, sorbitan fatty acid esters, polyoxyethylene ethers with sorbitan fatty acid esters, polyoxyethylene glycol esters with fatty or rosin acids, fatty alkylol amide condensates, calcium and amine salts of fatty alcohol sulfates, oil soluble petroleum sulfonates, or preferably mixtures of these emulsifying agents. Such emulsifying agents will comprise from about 1 to 10 weight percent of the total composition.

Thus, emulsifiable concentrates of the present invention will consist of from about 15 to about 50 weight percent active material, about 40 to 82 weight percent solvent, and about 1 to 10 weight percent emulsifier. Other additives such as spreading agents and stickers can also be included.

C. GRANULES AND PELLETS

Granules and pellets are physically stable, particulate compositions containing the active ingredients adhering to or distributed through a basic matrix of a coherent, inert carrier with microscopic dimensions. A typical particle is about 1 to 2 millimeters in diameter. Surfactants are often present to aid in leaching of the active ingredient from the granule or pellet.

The carrier is preferably of mineral origin, and generally falls within one or two types. The first are porous, absorptive, preformed granules, such as preformed and screened granular attapulgite or heat expanded, granular, screened vermiculite. On either of these, a solution of the active agent can be sprayed and will be absorbed at concentrations up to 25 weight percent of the total weight. The second, which are also suitable for pellets, are initially powdered kaolin clays, hydrated attapulgite, or bentonite clays in the form of sodium, calcium, or magnesium bentonites. Water-soluble salts, such as sodium salts, may also be present to aid in the disintegration of granules or pellets in the presence of moisture. These ingredients are blended with the active components to give mixtures that are granulated or pelleted, followed by drying, to yield formulations with the active component distributed uniformly throughout the mass. Such granules and pellets can also be made with 25 to 30 weight percent active component, but more frequently a concentration of about 10 weight percent is desired for optimum distribution. The granular compositions of this invention are most useful in a size range of 15–30 mesh.

The surfactant is generally a common wetting agent of anionic or nonionic character. The most suitable wetting agents depend upon the type of granule used. When preformed granules are sprayed with active material in liquid form the most suitable wetting agents are nonionic, liquid wetters miscible with the solvent. These are compounds most generally known in the art as emulsifiers, and comprise alkylaryl polyether alcohols, alkyl polyether alcohols, polyoxyethylene sorbitan fatty acid esters, polyethylene glycol esters with fatty or rosin acids, fatty alkylol amide condensates, oil solution petroleum or vegetable oil sulfonates, or mixtures of these. Such agents will usually comprise up to about 5 weight percent of the total composition.

When the active ingredient is first mixed with a powdered carrier and subsequently granulated, or pelleted, liquid nonionic wetters can still be used, but it is usually preferable to incorporate at the mixing stage one of the solid, powdered anionic wetting agents such as those previously listed for the wettable powders. Such agents will comprise from about 0 to 2 weight percent of the total composition.

Thus, the preferred granular or pelleted formulations of this invention comprise about 5 to 30 percent by weight active material, about 0 to 5 weight percent wetting agent, and about 65 to 95 weight percent inert material carrier, as these terms are used herein.

D. MICROCAPSULES

Microcapsules consist of fully enclosed droplets or granules containing the active materials, in which the enclosing material is an inert porous membrane, arranged to allow escape of the enclosed materials to the surrounding medium at controlled rates over a specified period. Encapsulated droplets are typically about 1 to 50 microns in diameter.

The enclosed liquid typically constitutes about 50 to 95% of the weight of the entire capsule, and may contain a small amount of solvent in addition to the active materials.

Encapsulated granules are characterized by porous membranes sealing the openings of the granule carrier pores, trapping the liquid containing the active compounds inside for controlled release. A typical granule size ranges from 1 millimeter to 1 centimeter in diameter. In agricultural useage, the granule size is generally about 1 to 2 ml in diameter. Granules formed by extrusion, agglomeration, or prilling are useful in the present invention as well as materials in their naturally occurring form. Examples of such carriers are vermiculite, sintered clay granules, kaolin, attapulgite clay, sawdust, and granular carbon.

Useful encapsulating materials include natural and synthetic rubbers, cellulosic materials, styrene-butadiene copolymers, polyacrylonitriles, polyacrylates, polyesters, polyamides, polyurethanes, and starch xanthates.

E. IN GENERAL

Each of the above formulations can be prepared as a package containing the herbicide together with the other ingredients of the formulation (diluents, emulsifiers, surfactants, etc.). The formulations can also be prepared by a tank mix method, in which the ingredients are obtained separately and combined at the grower site.

The compounds of the invention can be used in association (for example in the form of a mixture) with another herbicide.

Examples of such herbicides are:

a. benzo-2,1,3-thiadiazin-4-one-2,2-dioxides such as 3-isopropylbenzo-2,1,3-thiadiazin-4-one-2,2-dioxide (bentazon);

b. hormone herbicides, particularly the phenoxy alkanoic acids such as 4-chloro-2-methylphenoxy acetic acid (MCPA), 2-(2,4-dichlorophenoxy)propionic acid (dichloroprop), 2,4,5-trichlorophenoxyacetic acid (2,4,5-T), 4-(4-chloro-2-methylphenoxy)butyric acid (MCPB), 2,4-dichlorophenoxyacetic acid (2,4-D), 4-(2,4-dichlorophenoxy)butyric acid (2,4-DB), 2-(4-chloro-2-methylphenoxy)propionic acid (mecoprop), and their derivatives (e.g., salts, esters and amides);

c. 3-[4-(4-halophenoxy)phenyl]-1,1-dialkylureas such as 3-[4-(4-chlorophenoxy)phenyl]-1,1-dimethylurea (chlorophenoxy)phenyl]-1,1-dimethylurea (chloroxuron);

d. dinitrophenols and their derivatives (e.g., acetates) such as 2-methyl-4,6-dinitrophenol (DNOC), 2-t-butyl-4,6-dinitrophenol (dinoterb), 2-sec-butyl-4,6-dinitrophenol (dinoseb) and its ester, dinoseb acetate;

e. dinitroaniline herbicides such as N',N'-diethyl-2,6-dinitro-4-trifluoromethyl-m-phenylenediamine (dinitramine), 2,6-dinitro-N,N-dipropyl-4-trifluoromethylaniline (trifluralin) and 4-methylsulfonyl-2,6-dinitro-N,N-dipropylaniline (nitralin);

f. phenylurea herbicides such as N'-(3,4-dichlorophenyl)-N,N-dimethylurea (diuron) and N,N-dimethyl-N'-[3-(trifluoromethyl)phenyl]urea (flumeturon);

g. phenylcarbamoyloxyphenylcarbamates such as 3-[methoxycarbonylamino]phenyl-(3-methylphenyl)-carbamate (phenmedipham) and 3-(ethoxycarbonylamino)phenyl phenylcarbamate (desmedipham);

h. 2-phenylpyridazin-3-ones such as 5-amino-4-chloro-2-phenylpyradazin-3-one (pyrazon);

i. uracil herbicides such as 3-cyclohexyl-5,6-trimethyleneuracil (lenacil), 5-bromo-3-sec-butyl-6-methyluracil (bromacil) and 3-t-butyl-5-chloro-6-methyluracil (terbacil);

j. triazine herbicides such as 2-chloro-4-ethylamino-6-(i-propylamino)-1,3,5-triazine (atrazine), 2-chloro-4,6-di-(ethylamino)-1,3,5-triazine (simazine) and 2-azido-4-(i-propylamino)-6-methylthio-1,3,5-triazine (aziprotryne);

k. 1-alkoxy-1-alkyl-3-phenylurea herbicides such as 3-(3,4-dichlorophenyl)-1-methylurea (linuron), 3-(4-chlorophenyl)-1-methoxy-1-methylurea (monolinuron) and 3-(4-bromo-4-chlorophenyl)-1-methoxy-1-methylurea (chlorobromuron);

l. thiolcarbamate herbicides such as S-propyl dipropyl thiocarbamate (vernolate);

m. 1,2,4-triazin-5-one herbicides such as 4-amino-4,5-dihydro-3-methyl-6-phenyl-1,2,4-triazine-5-one (metamitron) and 4-amino-6-t-butyl-4,5-dihydro-3-methylthio-1,3,4-triazin-5-one (metribuzin);

n. benzoic acid herbicides such as 2,3,6-trichlorobenzoic acid (2,3,6-TBA), 3,6-dichloro-2-methoxybenzoic acid (dicamba) and 3-amino-2,5-dichlorobenzoic acid (chloramben);

o. anilide herbicides such as N-butoxymethyl-N-chloroacetyl-2',6'-diethylacetanilide (butachlor), the corresponding N-methoxy compound (alachlor), the corresponding N-i-propyl compound (propachlor) and 3',4'-dichloropropionanilide (propanil);

p. dihalobenzonitrile herbicides such as 2,6-dichlorobenzonitrile (dichlobenil), 3,5-dibromo-4-hydroxybenzonitrile (bromoxynil) and 3,5-diiodo-4-hydroxybenzonitrile (ioxynil);

q. haloalkanoic herbicides such as 2,2-dichloropropionic acid (dalapon) and trichloroacetic acid (TCA) and salts thereof;

r. diphenyl ether herbicides such as 4-nitrophenyl-2-nitro-4-trifluoromethylphenyl ether (fluorodifen), methyl-5-(2,4-dichlorophenoxy)-2-nitrobenzoate (bifenox), 2-nitro-5-(2-chloro-4-trifluoromethylphenoxy)-benzoic acid and 2-chloro-4-trifluoromethylphenyl-3-ethoxy-4-nitrophenyl ether;

s. aryloxyphenoxypropionic acids and their derivatives (salts, esters, amides and the like) such as methyl-2-(4-(2,4-dichlorophenoxy)-phenoxy]propionate (dichlorofopmethyl), methyl-2-[4-(4-trifluoromethylphenoxy)phenoxy]propionate (trifopmethyl); butyl-2-[4-(5-trifluoromethylpyridyl-2-oxy)phenoxy]propionate (fluazifop-butyl), methyl-2-[4-(3-chloro-5-trifluoromethylpyridyl-2-oxy)-phenoxy]propionate (haloxyfop-methyl) and ethyl-2-[4-(6-chlorobenzoxazolyl-2-oxy)-phenoxy]propionate (fenoxapropethyl);

t. substituted oxime ethers such as methyl 3-(1-allyloxyimino)-butyl-4-hydroxy-6,6-dimethyl-2-oxocyclohexane-3-ene carboxylate sodium salt (alloxdim-sodium), 2-[(1-ethoxyimino)butyl-5-(2-ethylthio)-propyl]-3-hydroxy-2-cyclohexen-1-one (sethoxydim); 2-(1-ethoxyimino)butyl-3-hydroxy-5-thian-3-ylcyclohex-2-enone (cycloxdim) and 2-[1-(3-chloroallyloxy)-butyl]5-(2-ethylthiopropyl)-3-hydroxycyclohex-2-enone (cloproxydim);

u. substituted sulfonyl ureas such as 1-(2-chlorophenylsulfonyl)-3-(4-methoxy-6-methyl-1,3,5-triazin-2-yl)-urea (chlorsulfuron), methyl-2-(((((4,6-dimethyl-2-pyrimidinyl)amino)carbonyl)amino)sulfonyl)-benzoate (sulfometuron methyl), 2-[3-(4-methoxy-6-methyl-1,3,5-triazin-2-yl)ureidosulfonyl]benzoic acid (metsulfuron methyl) and methyl 2-(((4,6-dimethoxypyrimidin-2-yl)aminocarbonyl)aminosulfonylmethyl)benzoate (Londax).

v. substituted imidazoles such as 2-(4,5-dihydro-4-isopropyl-4-methyl-5-oxoimidazol-2-yl)quinoline-3-carboxylic acid (imazaquin); methyl-2-(4-isopropyl-4-methyl-5-oxo-2-imidazolin-2-yl)-p-toluate (imazamethabenz), 2-(4-isopropyl-4-methyl-5-oxo-2-imidazolin-2-yl)nicotinic acid isopropylamine salt (imazpyr-isopropylammonium) and 5-ethyl-2-(4-isopropyl-4-methyl-5-oxo-2-imidazolin-2-yl)nicotinic acid (imazethapyr);

w. substituted phosphonic and phosphinic acids such as N-phosphonomethylglycine (glyphosate) and its derivatives, and DL-homoalanin-4-yl (methyl) phosphonic acid (phosphinothricin);

x. bipyridylium diquaternary salts such as salts of the 1,1'-dimethyl-4,4'-bipyridylium ion (paraquat ion) and the 1,1'-ethylene-2,2-bi-pyridylium ion (diquat ion); and y. other known herbicides, including diphenamid, napthalam, ethofumesate, difenzoquat, flamprop-M-isopropyl, oxadiazon, bromofenoxim, pyridate, pyrazolate, daimuron, napropamide, piperophos, thiocarbazil, phenothiol, flurenol, norflurazon, benzoylprop-ethyl, methabenzthiazuron, barban, propyzamide, carbetamide, tebutam, diflufenican and isoxaben.

In general, any conventional method of application can be used. The locus of application can be soil, seeds, seedlings, or the actual plants, as well as flooded fields. Post-emergent application is preferred. Dusts and liquid compositions can be applied by the use of powder dusters, boom and hand sprayers, and spray dusters. The compositions can also be applied from airplanes as dusts and sprays because they are effective in very low dosages. In order to modify or control the growth of germinating seeds or emerging seedlings, as a typical example, the dust and liquid compositions are applied to the soil according to conventional methods and are distributed in the soil to a depth of at least one-half inch below the soil surface. It is not necessary that the phytotoxic compositions be admixed with the soil particles. Instead, these compositions can be applied merely by spraying or sprinking the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional metans such as discing, dragging or mixing operations.

The herbicide compositions can also be applied to the soil through irrigation systems. According to this technique, the compositions are added directly to irrigation water immediately prior to irrigation of the field. This technique is applicable in all geographical areas regardless of rainfall, since it permits supplementation of the natural rainfall at critical stages of plant growth. In a typical application, the concentration of the herbicide composition in the irrigation water will range from about 10 to 150 parts per million by weight. The irrigation water can be applied by the use of sprinkler systems, surface furrows, or flooding. Such application is most effective done before the weeds germinate, either early in the spring prior to germination or within two days after cultivation of the field.

The amount of the present composition which constitutes a herbicidally effective amount depends upon the nature of the seeds or plants to be controlled. The rate of application of active ingredient varies from about 0.01 to about 50 pounds per acre, preferably about 0.1 to about 25 pounds per acre with the actual amount depending on the overall cost and the desired results. It will be readily apparent to one skilled in the art that compositions exhibiting lower herbicidal activity will require a higher dosage than more active compounds for the same degree of control.

What is claimed is:

1. A compound having the formula

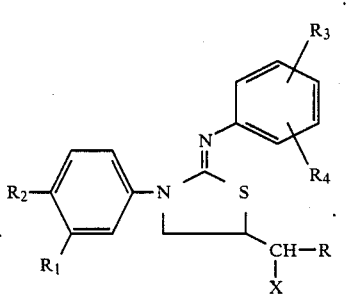

wherein
R is hydrogen or methyl;
$R_1$ is halo, nitro, cyano, $C_1$-$C_4$ alkyl, $C_1$-$C_4$ alkoxy, perhalomethyl, difluoromethyl, pentafluoroethyl, trifluoromethylthio, difluoromethoxy, trifluoromethoxy, tetrafluoroethoxy, methylsulfonyl, $C_1$-$C_4$ alkyloxyiminomethyl, benzyloxyiminomethyl, 1-($C_1$-$C_4$ alkyl)oxyiminoethyl or 1-benzyloxyiminoethyl;
$R_2$ is hydrogen or halo;
$R_3$ and $R_4$ are independently hydrogen, halo, nitro, cyano, $C_1$-$C_4$ haloalkyl, $C_1$-$C_4$ alkyl, $C_1$-$C_4$ fluoroalkoxy, $C_1$-$C_4$ alkoxy or $C_1$-$C_4$ alkylthio; and
X is hydrogen or halogen.

2. A compound according to claim 1 wherein $R_2$ is hydrogen.

3. A compound according to claim 1 wherein $R_4$ is hydrogen.

4. A compound according to claim 3 wherein $R_3$ is located at the 2-position on the phenyl ring.

5. A compound according to claim 3 wherein $R_3$ is located at the 3-position on the phenyl ring.

6. A compound according to claim 3 wherein $R_3$ is located at the 4-position on the phenyl ring.

7. A compound according to claim 3 wherein $R_3$ is halo, nitro, cyano, methyl, methoxy, trifluoromethyl, trifluoromethoxy or methylthio.

8. A compound according to claim 1 wherein $R_4$ is hydrogen, halo or methyl.

9. A compound according to claim 1 wherein $R_1$ is halo, cyano, trifluoromethyl or trifluoromethylthio.

10. The compound of claim 2 wherein R is methyl, $R_1$ is trifluoromethyl, $R_3$ is p-cyano, $R_4$ is hydrogen and X is hydrogen.

11. The compound of claim 2 wherein R is hydrogen, $R_1$ is trifluoromethyl, $R_3$ is m-trifluoromethyl, $R_4$ is hydrogen and X is hydrogen.

12. The compound of claim 2 wherein R is methyl, $R_1$ is trifluoromethyl, $R_3$ is p-chloro, $R_4$ is hydrogen and X is hydrogen.

13. The compound of claim 2 wherein R is hydrogen, $R_1$ is trifluoromethyl, $R_3$ is m-nitro, $R_4$ is hydrogen and X is chlorine.

14. The compound of claim 2 wherein R is hydrogen, $R_1$ is cyano, $R_3$ is m-chloro, $R_4$ is hydrogen and X is hydrogen.

15. The compound of claim 2 wherein R is methyl, $R_1$ is chloro, $R_3$ is p-cyano, $R_4$ is hydrogen and X is hydrogen.

16. The compound of claim 2 wherein R is hydrogen, $R_1$ is chloro, $R_3$ is m-bromo, $R_4$ is hydrogen and X is hydrogen.

17. The compound of claim 2 wherein R is methyl, $R_1$ is trifluoromethyl, $R_3$ is p-trifluoromethyl, $R_4$ is hydrogen and X is hydrogen.

18. The compound of claim 2 wherein R is methyl, $R_1$ is trifluoromethyl, $R_3$ is m-chloro, $R_4$ is p-fluoro and X is hydrogen.

19. The compound of claim 2 wherein R is hydrogen, $R_1$ is trifluoromethyl, $R_3$ is o-fluoro, $R_4$ is p-fluoro and X is hydrogen.

20. An herbicidal composition which comprises: (a) an herbicidally effective amount of a compound according to claim 1 and (b) an herbicidally antidote inert dilutent or carrier.

21. A method for controlling undesirable weed pests which comprises applying to the locus where control is desired an herbicidally effective amount of a compound according to claim 1.

* * * * *

UNITED STATES PATENT AND TRADEMARK OFFICE
CERTIFICATE OF CORRECTION

PATENT NO. : 4,913,722
DATED : April 3, 1990
INVENTOR(S) : Frank X. Woolard, Eugene G. Teach and Jeffery T. Springer It is certified that error appears in the above-identified patent and that said Letters Patent is hereby corrected as shown below:

In Column 38, line 58, delete the word "antidote".

In Column 38, line 59, "dilutent" should read --- diluent ---.

On the title page, item (75) inventors, delete;
"Raymond A. Felix, Richmond" from the Inventors. List Frank X. Woolard first, therefore, Frank X. Woolard, Eugene G. Teach and Jeffery T. Springer.

Signed and Sealed this

Fifteenth Day of March, 1994

BRUCE LEHMAN

Attest:

Attesting Officer     Commissioner of Patents and Trademarks